United States Patent [19]
Heitz et al.

[11] Patent Number: 5,798,112
[45] Date of Patent: Aug. 25, 1998

[54] PHOTOTOXIC INSECTICIDAL COMPOSITION AND METHOD FOR CONTROLLING INSECT POPULATIONS

[75] Inventors: James R. Heitz, Starkville, Miss.; Robert L. Mangan; Daniel S. Moreno, both of Weslaco, Tex.

[73] Assignees: The United States of America as represented by the Secretary of Agriculture, Washington, D.C.; Photodyne International Inc., Linthicum, Md.

[21] Appl. No.: 717,225

[22] Filed: Sep. 26, 1996

Related U.S. Application Data

[63] Continuation-in-part of Ser. No. 543,475, Oct. 16, 1995, Pat. No. 5,676,959, which is a continuation-in-part of Ser. No. 352,925, Dec. 9, 1994, abandoned.

[51] Int. Cl.$^6$ .................................................. A01N 25/02
[52] U.S. Cl. .................... 424/405; 424/406; 424/407; 424/410; 424/420; 514/455
[58] Field of Search ................. 424/405, 406–408, 424/410, 419, 420; 514/84, 455

[56] References Cited

U.S. PATENT DOCUMENTS

| | | | |
|---|---|---|---|
| 3,937,826 | 2/1976 | Harris | 424/219 |
| 4,160,824 | 7/1979 | Inazuka et al. | 424/84 |
| 4,205,066 | 5/1980 | Hennart et al. | 424/84 |
| 4,320,140 | 3/1982 | Crounse et al. | 424/283 |
| 4,647,578 | 3/1987 | Crounse et al. | 514/454 |
| 4,855,133 | 8/1989 | Kamei et al. | 424/84 |
| 4,937,082 | 6/1990 | Sawhill | 426/69 |

OTHER PUBLICATIONS

Heitz and Downum—ACS Symposium Series 616 "Light--Activated Pest Control" Symposium on Apr. 2–6, 1995 Published by ACS, Washington, DC.

Mangan and Moreno—Development of Phloxine B and Uranine Bait for Control of Mexican Fruit Fly, pp. 115–126 (article received Aug. 30, 1995)–ACS Symposium Series 616.

Moreno and Mangan—Supplement—Responses of the Mexican Fruit Fly (Diptera: Tephritidae) to Two Hydrolyzed Proteins and Incorporatoin of Phloxine B to Kill Adults, pp. 257–279 (article received Oct. 31, 1995)—ACS Synposium Series 616.

Lim A et al. Revistado Societdis–Braziletra de Zootenia (1983) vol. 12, #2 pp. 187–199.

*Primary Examiner*—Neil S. Levy
*Attorney, Agent, or Firm*—Leonard Bloom

[57] ABSTRACT

A phototoxic insecticidal composition includes at least one photoactive dye, an attractant bait composition and/or feeding stimulant and at least one adjuvant, whereby the adjuvant interacts with the photoactive dye and insect membranes to alter the toxicity of the composition once ingested by the insect. More specifically, the composition is directed to killing the Mexican fruit fly.

14 Claims, 6 Drawing Sheets

TYPICAL COMPOSITION (% EXCEPT AS INDICATED)

| | E802†<br>AS IS | E804‡<br>AS IS |
|---|---|---|
| PROTEIN<br>(GUARANTEED MINIMUM) | 20.0 | 18.0 |
| PROTEIN - AVERAGE<br>- RANGE | 22.0<br>20.0 – 25.0 | 20.0<br>18.0 – 22.0 |
| ALANINE | 1.8 | 1.5 |
| ARGININE | 1.1 | 0.9 |
| ASPARTIC ACID | 1.4 | 1.1 |
| CYSTINE | 0.8 | 0.7 |
| GLUTAMIC ACID | 3.5 | 2.8 |
| GLYCINE | 1.1 | 0.9 |
| HISTIDINE | 0.7 | 0.6 |
| ISOLEUCINE | 0.7 | 0.6 |
| LEUCINE | 2.0 | 1.6 |
| LYSINE | 0.8 | 0.7 |
| METHIONINE | 0.5 | 0.4 |
| PHENYLALANINE | 0.8 | 0.7 |
| PROLINE | 2.0 | 1.6 |
| SERINE | 1.0 | 0.8 |
| THREONINE | 0.9 | 0.7 |
| TRYPTOPHAN | 0.05 | 0.04 |
| TYROSINE | 0.5 | 0.4 |
| VALINE | 1.2 | 1.0 |

† MAZOFERM E802 IS SHIPPED IN LIQUID FORM, AND CONTAINS APPROXIMATELY 48% SOLIDS. SPECIFIC GRAVITY IS 1.25, PH 3.7 - 4.2, LACTIC ACID 10 – 13%.

‡ MAZOFERM "L" E804, A LOWER VISCOSITY PRODUCT, CONTAINS 40 – 45% SOLIDS AND AN 18% PROTEIN LEVEL.

FIG. 5A

TYPICAL COMPOSITION (% ACCEPT AS INDICATED)

|  |  | E802† AS IS | E804‡ AS IS |
|---|---|---|---|
| BETA-CAROTENE | (MG/LB) | 0 | 0 |
| BIOTIN | (MG/LB) | 0.15 | 0.13 |
| CHOLINE | (MG/LB) | 1590 | 1270 |
| INOSITOL | (MG/LB) | 2730 | 2203 |
| NIACIN | (MG/LB) | 38 | 32 |
| PANTOTHENIC ACID | (MG/LB) | 6.8 | 5.5 |
| PYRIDOXIDE | (MG/LB) | 4.0 | 3.2 |
| RIBOFLAVIN | (MG/LB) | 2.7 | 2.2 |
| THIAMINE | (MG/LB) | 1.3 | 1.0 |
| TOTAL ASH |  | 7.8 | 6.3 |
| CALCIUM |  | 0.14 | 0.05 |
| COPPER | (MG/LB) | 7.0 | 5.5 |
| IRON | (MG/LB) | 50 | 39 |
| MANGANESE | (MG/LB) | 11.0 | 8.6 |
| MAGNESIUM | (MG/LB) | 0.58 | 0.45 |
| PHOSPHORUS | (MG/LB) | 1.8 | 1.4 |
| POTASSIUM | (MG/LB) | 2.8 | 1.5 |
| SODIUM | (MG/LB) | 0.11 | 0.09 |
| CHLORIDE |  | 0.43 | 0.34 |
| SELENIUM | (MG/LB) | 0.16 | 0.13 |
| SULFUR | (MG/LB) | 0.59 | 0.46 |
| ZINC | (MG/LB) | 30.0 | 23.5 |
| METABOLIZE ENERGY | (KCAL/LB) | POULTRY 707 | POULTRY 569 |
|  | KCAL/KG | POULTRY 1568 | POULTRY 1258 |
| T.D.N. |  | 40 | 32.3 |
| NITROGEN FREE EXTRACT |  | 18 | 14.5 |
| DENSITY | (LBS/CU.FT) | 78.5 | 74.8 |
|  | (LBS/GAL) | 10.5 | 10.0 |

† MAZOFERM E802 IS SHIPPED IN LIQUID FORM, AND CONTAINS APPROXIMATELY 48% SOLIDS. SPECIFIC GRAVITY IS 1.25, PH 3.7 – 4.2, LACTIC ACID 10 – 13%.

‡ MAZOFERM "L" E804, A LOWER VISCOSITY PRODUCT, CONTAINS 40 – 45% SOLIDS AND AN 18% PROTEIN LEVEL.

FIG. 5B

PHOTOTOXIC INSECTICIDAL COMPOSITION AND METHOD FOR CONTROLLING INSECT POPULATIONS

This application is a continuation-in-part application Ser. No. 08/543,475 filed Oct. 16, 1995, now U.S. Pat. No. 5,676,959 which was a continuation-in-part application of patent application Ser. No. 08/352,925 filed on Dec. 9, 1994, now abandoned. All disclosures are incorporated herein by reference.

BACKGROUND OF THE INVENTION

1. Field of the Invention

The present invention relates to insecticidal compositions and, more particularly, to an insecticidal composition including a photoactive dye which, when ingested by an insect, becomes phototoxic and kills the insect.

2. Description of the Related Art

Many species of insects, from insect groups such as flies, worms, ants, beetles and the like, present a serious threat to agricultural industries throughout the world. In fact, entire harvests have been lost due to insect infestation, costing farmers hundreds of millions (if not billions) of dollars each year. Further, insects of many types present a nuisance and, in some instances, a health risk to humans and many animals. Accordingly, from both an economic standpoint and a health standpoint, it is essential to control the population of certain species of insects from many different insect groups.

For instance, fruit flies of the family Tephritidae include several species that are major pests of agriculture throughout the world and represent a serious threat to U.S. and foreign agricultural industries. The U.S. Department of Agriculture (USDA), Animal and Plant Health Inspection Service (APHIS), in cooperation with other federal and state organizations, has conducted a number of programs to eradicate some species of fruit files when these insects have been introduced to the U.S. mainland. These programs generally have employed an integrated pest management approach to eradication. Many recent programs have involved the application of malathion bait spray to effectively lower fly populations in the infested area, followed by a release of sterile flies. However, aerial applications of the bait spray over populated areas to control infestations of fruit flies have been controversial, and concerns about adverse health effects from exposure to malathion bait spray have been raised by residents of treated neighborhoods.

The currently used malathion bait system, which contains the main ingredients NuLure and malathion for control of Mexican fruit flies, uses an attractant (acid hydrolyzed protein) and a contact insecticide (malathion). This system has had a bad public perception. The malathion bait system not only damages paint finishes on cars but also, because of the high concentration of insecticides (10%–20%) in the bait, it has an extremely detrimental effect on other, beneficial insect groups that may contact the bait surface or be exposed to the volatile fumes. The United States government has mandated that certain currently listed pesticides, such as malathion, should have a more restricted use pattern. The Environmental Protection Agency has specifically requested that safer pesticides be developed for use in the agricultural sector.

In the past, xanthene dyes and other photoactive dyes have been used to kill certain species of insects. In particular, the U.S. patent to Crounse et al, U.S. Pat. No. 4,160,824, discloses the mixture of at least one insecticidally active water soluble xanthene dye and an insecticidally inactive water soluble xanthene dye. Crounse et al teaches that the mixture of these dyes is synergistically better than either of the dyes alone.

The addition of a surfactant to a photoactive dye composition is taught by Crounse et al, U.S. Pat. No. 4,647,578. Crounse et al '578 teaches the application of a solid water insoluble dye mixture over an aqueous surface of a mosquito breeding area. The purpose of the surfactant is specifically aimed at a more complete coverage of the dye over the water surface to make it more likely that mosquito larvae will encounter the individual dye particles and mistake them for detritus, the mosquito's normal food, and consume it. Crounse et al '578 does not teach that the surfactant enhances the toxicity of the dyes when consumed by the target insect.

The patent to Inazuka et al, U.S. Pat. No. 4,160,824 teaches the use of a surfactant to emulsify a water insoluble pesticide, such as malathion, so that it becomes soluble in an aqueous medium. However, Inazuka does not disclose photoactive dyes among his disclosed insecticides.

While xanthene dyes have been known to be effective for use in insecticides as evidenced by the patents to Crounse et al, only a few dyes have been previously found to be effective. Experimental data has shown that the efficacy of these known xanthene dyes, when used alone or in combination with an attractant, is limited and is only effective on certain insects. Further, in many cases, the insect must consume a substantial quantity of the dye composition to reach concentration levels which are sufficient to cause damage and kill the insect.

SUMMARY OF THE INVENTION

In the quest for these aforementioned safer pesticides, it has been unexpectedly discovered that dye-sensitized photoactive substances can be effectively utilized as the active ingredient in insecticides for use in a bait station or as a bait spray component which targets insects of the family Tephritidae, and specifically Mexican fruit flies and similar insects. The preferred photoactive dye for these purposes is a halogenated xanthene such as phloxine B or a mixture of a halogenated xanthene and fluorescein. Other known xanthene dyes which could be used are, for example, erythrosin B and rose bengal. Photoactive dyes (including phloxine B) are more fully described in the U.S. Patents to Crounse and Heitz, U.S. Pat. No. 4,647,578 and U.S. Pat. No. 4,320,140, the subject matter of which is incorporated herein by reference. When employing halogenated xanthene dyes, light activated toxicity is especially marked with respect to Mexican fruit flies. The photoactive dye ingredient of the present invention is effective due to the release of light induced excited singlet oxygen molecule free radicals within the body of the insect which has ingested the composition containing the dye. Due to its small proportionate body mass, the dose of light is fatal to the insect.

Although being extremely toxic with respect to the targeted Mexican fruit fly, the preferred dyes of the instant invention are non-toxic to humans, most mammals and nontargeted insects. This is a substantial advance in the industry, as prior art pesticides which were adopted for the purpose of controlling fruit fly populations, namely Malathion, have posed health risks to humans. Because Malathion is highly penetrable and invades cells very quickly upon contact, it is highly potent as a poison, both to insects and nontargeted species. The present invention, on the other hand, is directed to an active ingredient which is toxic to the targeted Mexican fruit fly, not due to cell penetration, as malathion, but rather due to ingestion and exposure to a quantity of light which is fatal to the fly. The effect of the same quantity of exposure to a human or other mammal would be negligible. In this regard, the compound phloxine B (2', 4', 5', 7'-tetrabromo-4,5,6,7, tetrachlorofluorescein) has been consumed by humans for decades. It is registered as D&C Red 28 as a drug and cosmetic additive and has been included in such commercially available products as Pepto Bismol. In fact, the intrinsic toxicity of Malathion is 62.5 times greater than that of phloxine B as measured by acute LD50 in rats.

Additionally, unlike Malathion which kills any insect merely upon contact, even nontargeted species such as honeybees, the photoactive dye ingredient of the present invention is not harmful unless ingested by the insect. Indeed, the skin penetrability of phloxine B has been calculated to be about 87 times lower than that of Malathion by octanol/water partition coefficient analysis conducted at the USDA.

Furthermore, because the active xanthene dye component is light-activated, a much smaller quantity is necessary to provide the desired effect. Moreover, contrary to the prior art broad spectrum pesticides which have a half-life on the order of months or even years, the xanthene based ingredient will exhibit a half-life in the environment of hours or days and will naturally photodegrade. Thus, the use of photoactive dyes not only provides an extremely high kill rate when introduced in the targeted Mexican fruit fly population, but additionally poses little or no risk for use in the agriculture industry.

An additional benefit which is offered by the use of xanthene based dyes as the active ingredient in pesticide compositions, resides in the fact that, after ingestion, the dye does not kill the insect immediately. This allows the insect which has ingested the pesticide to effectively transfer some quantity of the pesticide among other conspecific insects in the population through excretion, regurgitation or "gift-offering". Therefore, substantially more insects will be eliminated due to the transfer of the toxic material between flies.

The present insecticidal composition further contemplates the inclusion of an enzymatic hydrolyzed protein as an attractant. The attractant should be substantially free of sodium and calcium salts. A preferred protein of this type is the commercially available product Mazoferm, a condensed fermented corn extractive. Mazoferm is supplied by CornProducts, a unit of CPC International, Inc., and is fully described in the company's Product Data Sheet for Mazoferm. The attractant ability of Mazoferm specifically toward the Mexican fruit fly is marked and equally pronounced for both sexes of the Mexican fruit fly. Further, the feeding rate is increased substantially by the additional incorporation of simple sugars, such as fructose to the composition. The composition may optional include anti-foaming agents and other adjuvants to increase the permeability of the ingested dye within the gut of the insect.

It is, therefore, an important object of the present invention to provide a pesticide that is toxic only when ingested by certain families of insects and, in particular, the Mexican fruit fly.

It is a further object to provide a pesticide that has a delayed toxicity to the insect.

A still further object lies in the provision of a pesticide which has minimal detrimental effect on the behavior of the insect between the period of ingestion and the onset of toxicity.

A still further object of the present invention lies in the provision of an insecticidal composition which is highly attractive to both sexes of the Mexican fruit fly.

A yet further object of the present invention resides in the provision of an insecticidal composition which contains no feeding inhibitors that may limit feeding or may induce a learned behavior to avoid the bait.

It is a further object of the present invention to provide an insecticidal composition comprising at least one photoactive dye, wherein the toxicity of the photoactive dye is controlled for different target insects using one or more selected adjuvants.

It is still a further object of the present invention to provide an insecticidal composition wherein the rate of kill and time of kill of a particular species of an insect group can be controlled and manipulated.

It is yet a further object of the present invention to provide an insecticidal composition which is phototoxic to a specific targeted insect species and yet non-toxic to other insect groups as well as humans, animals and plants.

It is still a further object of the present invention to provide an insecticidal composition which is environmentally safe and which has no detrimental effects beyond the toxic efficacy to a specific targeted insect species.

It is yet a further object of the present invention to provide an insecticidal composition comprising at least one photoactive dye and wherein the composition functions inside of a target insect to materially effect the toxicity of the photoactive dye in the insect.

It is still a further object of the present invention to provide an insecticidal composition comprising at least one photoactive dye and a specific attractant and/or insect stimulant to target specific species within of an insect group so that the particular species will consume the composition.

It is yet a further object of the present invention to provide an insecticidal composition comprising a specific composition of elements including at least one selected photoactive dye, a selected attractant (bait) and/or feeding stimulant to target one or more specific species of insects and at least one selected adjuvant to control the toxicity of the photoactive dye or dyes once consumed by the target insect(s), wherein the composition is not attractive to other non-target insects; thereby assuring that beneficial insects will not be harmed or killed by the insecticidal composition.

Lastly, it is an object of the present invention to provide an insecticidal composition which incorporates a bait that stimulates feeding and induces engorgement by the insects.

These together with other objects of the invention, are pointed out with particularity in the following detailed description and claims annexed hereto and forming part of this disclosure.

Through extensive experimental testing and observation, the inventors hereof have determined that a large number of compounds in an array of chemical groups are phototoxic to insects, and the activity of these dyes can be effectively regulated to increase insecticidal efficacy through the use of adjuvants and other additives. The efficacy of the observed toxic activity has been unexpectedly shown to be related to a complex interaction between the dye characteristics and the adjuvant chemistry. In a series of tests it was found that without the adjuvants, the majority of the dyes tested had little or no potential as insecticides because they would need to be consumed at concentrations that would inhibit feeding or, they would be excreted from the insect's body before they reached sufficient concentration to damage the insect.

The experiments conducted by the inventors hereof have determined that the variation in the killing efficacy (dose and time delay) of the photoactive dyes can be attributed to a much greater extent (and therefore manipulated) by use of particular adjuvants and additives rather than by varying concentrations of the dyes or by interchanging dyes.

The present invention is directed to an insecticidal composition which combines one or more selected photoactive dyes with a selected attractant (bait) and a selected adjuvant, wherein the selected adjuvant interacts with the insect membranes to alter the transport of the dyes through the insect body to susceptible target organs. Accordingly, through specific interactions of the photoactive dye, the selected adjuvant, and the insect membranes, there is a significantly increased, controllable and previously unknown toxic effect that results in mortality of the particular targeted insect.

With the foregoing in mind, it is a primary object of the present invention to provide a phototoxic insecticidal composition comprising at least one photoactive dye, an attractant and/or insect stimulant, and at least one adjuvant selected from a group of adjuvants, wherein the adjutant alters the toxic activity of the photoactive dye.

This invention is particularly directed to compositions having enhanced toxic effects on the Mexican fruit fly (Diptera: Tephritidae), and particularly to kill adult Mexican fruit fly.

The inventors have made a series of discoveries wherein insecticidal formulations have been enhanced.

The inventors have discovered in laboratory tests that certain hydrolyzed proteins are more attractive to the fruit fly than unhydrolyzed proteins. They have also discovered that in the field when NuLure was tested against Mazoferm (both hydrolyzed proteins), Mazoferm was found to be more attractive to the Mexican fruit fly. In terms of consumption Mazoferm was consumed more than NuLure. This is an important consideration since photoactive dyes, unlike malathion, have to be consumed in adequate amounts in order to be toxic.

The inventors have tested a series of dyes with hydrolyzed protein baits. For example, phloxine B was tried with Mazoferm and found to be an effective insecticide. The effect of uranine added to phloxine B and hydrolyzed protein bait did not substantially enhance fly death.

The inventors have further found certain beneficial adjuvants which enhance insecticidal activity of the dyes. These adjuvants are agents which are commercially available and are formulated to break interfacial tension. A preferred adjuvant is SM-9 which is a proprietary blend of linear secondary alcohols reacted with ethylene oxide 99.97% (SMI, Valdosta, Ga.). More specifically SM-9, useful for enhancing the activity of the photoactive dyes, is a nonionic surfactant, namely an alkyloxypolyethyleneoxyethanol of the chemical formula

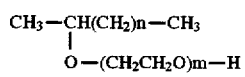

wherein n is from 9 to 15 and m is from 3 to 40. The surfactant is disclosed in U.S. Pat. No. 5,026,734. SM-9 was used in a composition of Mazoferm and fructose along with phloxine B. Experimental data shows that SM-9 greatly enhances the lethal effect of phloxine B on flies. Ancillary tests conducted found that SM-9 alone was not innately toxic.

The inventors have also found other photoactive dyes, besides phloxine B to be effective insecticides when incorporated into compositions containing SM-9. In addition, the inventors have also found that adjuvants other than SM-9 are effective activity enhancers.

The addition of vegetable oil has been shown to further enhance insecticidal activity. Moreover, the addition of ammonium compounds and acetic acid, respectively, have been shown to enhance insecticidal activity.

BRIEF DESCRIPTION OF THE DRAWINGS

FIGS. 5A and 5B are charts showing the typical composition of Mazoferm®.

DETAILED DESCRIPTION OF THE PREFERRED EMBODIMENTS

Figure 1:
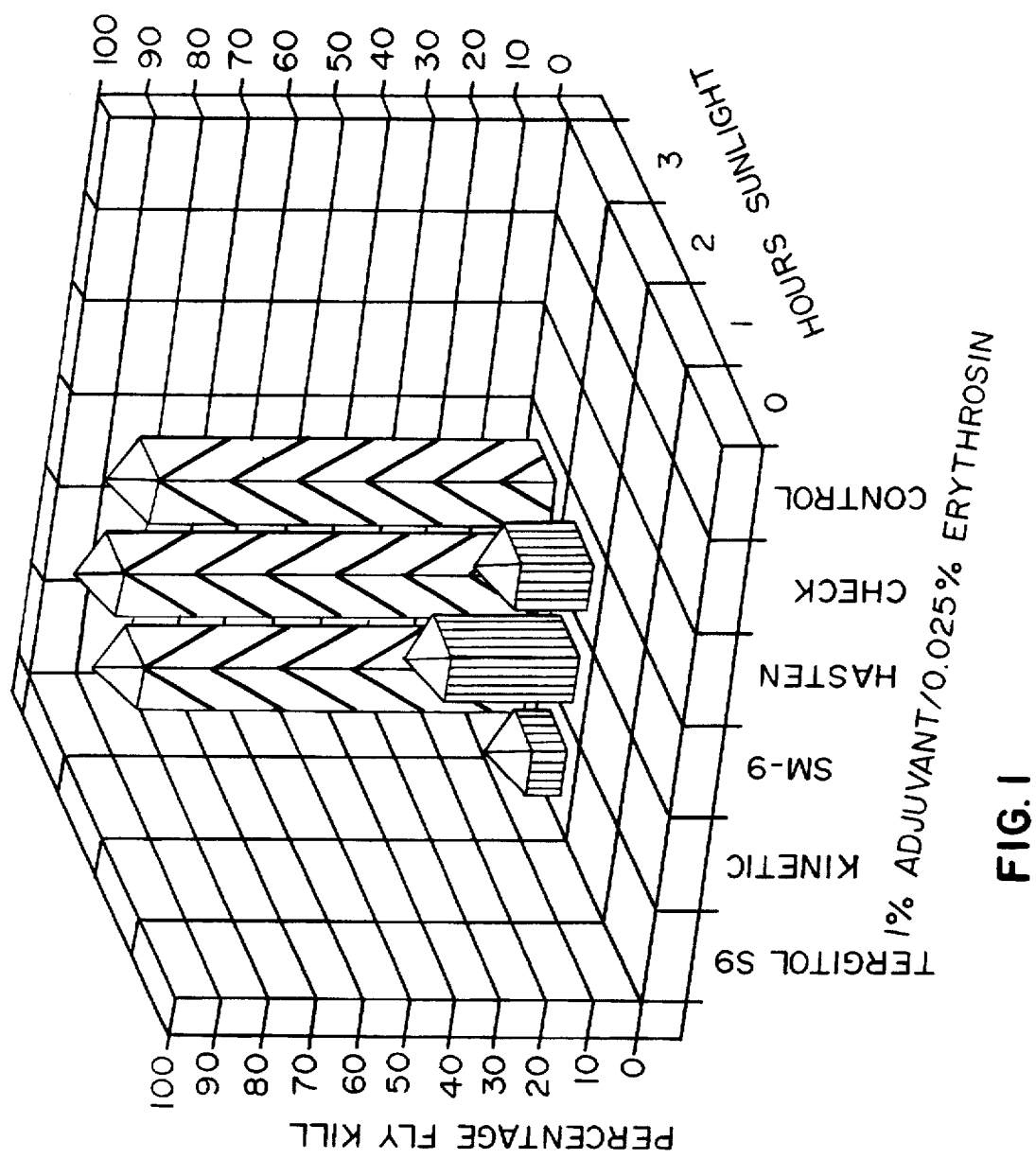
FIGS. 1 and 2 show that time delay from exposure to light to the onset of mortality was dependent on the interaction of the specific dye and adjustment.

The present invention relates to a bait system which takes advantage of several observations previously made that fruit flies tend to feed in groups, that adult flies in wild populations are protein starved during the ages of 4–12 days (sexual maturation), and that regurgitation and feeding between pairs or among groups of adult flies is an integral part of mating behavior.

Phloxine B (Red Dye #28) or (phloxine B+fluorescein) are toxic to the Mexican fruit fly in extremely low doses (LD90=<0.1 gram per liter) in sugar water. Additionally, the previously utilized bait, NuLure (acid hydrolyzed protein), is not palatable to Mexican fruit flies. The simple substitution of a stomach poison for malathion in NuLure spray formulation does not reduce fruit fly populations in the field or in laboratory cages. Thus, to achieve optimum results the use of an alternate bait or attractant formulation was required. It has been found under field conditions in south Texas both sexes of Mexican fruit flies are attracted to feeding stations containing an attractant formulation (Mazoferm) that consists of enzymatically hydrolyzed corn protein. This hydrolyzed protein contains virtually no salts (of sodium or calcium) that are found in NuLure. Mazoferm does not inhibit feeding by both sexes of Mexican fruit fly. Additionally, the feeding rate can be increased several fold by the addition of simple sugars to the formulation. The formulation may also be improved by adding anti-foaming agents to the mixture as well as other adjuvants to increase gut permeability of the formulation once it is ingested by the insect.

Mazoferm is described as a condensed, fermented corn extract. According to Hull, S. R., Yun Yang, B., Venzke, D., Kulhavy, K., and Mongomery, R. 1996. "Composition of Corn Steep Water during Steeping" J. Agric. Food Chem 44, 1857–1863, the "late" or "heavy" steepwaters are composed of 112.2–149.1 (g/L) dry weight with total carbohydrate ranging from 8.8 to 17.2 g/L, total amino acids from 33.1 to 62.6 g/L, and total lipids from 0.036 g/L to non-detectable content.

Mazoferm® condensed fermented corn extractives are produced in the corn wetmilling process when the dry corn is soaked (steeped) in a warm dilute sulfurous acid solution. During the process, the grain solubles are released and undergo a mild lactic acid fermentation from naturally occurring microorganisms. (See FIG. 5A and 5B).

The effect of the light activated photodye ingredient is especially pronounced with respect to Mexican fruit flies because these flies feed mostly early in the morning (1–2 hours after daybreak). The flies which feed on the toxic formulation of the present invention die during peak daylight hours. Ingestion of the dye by the fruit flies results in engorgement of the gut of flies under conditions with alternative natural food sources on the trees. The engorged flies leave the feeding site and engage in apparently normal behavior including regurgitation and reconsumption of drops of the toxic bait.

Furthermore, the estimated mortality rate of flies greatly exceeds the numbers observed feeding on the bait which indicates that a large portion of the mortality is due to transfer of the toxic material between flies.

The following examples describe various innovative aspects of the present invention.

Efficacy of the photoactive dye formulation of the present invention was tested under field conditions on mature, fruit-bearing grapefruit trees (Table 3). Adult Mexican fruit flies were released in the cages either as they emerged from pupae (replicates 1, 2) or as 3–4 day old adults (replicates 3–7). Trees were heavily infested with various homopteran pests (scale insects, mealybugs) and mites during the first two replicates. The inventors attempted to control these pests at about the level found in a commercial orchard for the later tests. There were four separated sections of the cage each with one tree. The sections were separated from each other by a third section in the center of the cage so there were no direct entrances from one section to another. In each test, two sections were treated with a dye-bait solution (dye treatment) and two sections with the bait alone (control). Water was provided by wicks protruding from plastic containers in all tests. For sequential tests the two treatments were rotated with identical treatments located diagonally from each other in the cage. In all tests the dye was the mixture of phloxine B and fluorescein. The bait consisted of a formulation of 70% Mazoferm, 20% fructose, 0.1% SM-9 and 0.5% or 2.0% dye with the remainder water.

Baits were not applied to the trees in any tests. In the first test a cup with ca 100 ml of bait was suspended below a cap (for shade and rain protection) as the feeding site. In all other tests, baits (with or without dye) were soaked into sponge sheets, the sponges were stapled to rigid plastic (yellow) backing and folded to make a roof structure with the sponge in the underside. The stations were hung in the trees. Flies were observed to feed on the bait, no flies were ever observed to get stuck on the surface of the sponges. We tested various numbers and shapes of feeding stations keeping the total surface area and amount of bait constant. We could not discover any effect due to these factors.

The procedure was to release flies on day one, allow them to feed on the bait stations and freely move about the cage for 4.5 days, then remove the stations and water. During tests 1 and 2 we released 2,000 flies per cage as they emerged, for tests 3–7 we released 3000 4–6 day old flies. The sex ratio was about 1:1 male to female for the flies. Flies were provided only sugar and water prior to release. On the afternoon of the 5th day, 2 McPhail type traps with ammonium acetate or other attractants were placed in each cage (identical traps and attractants were used in each cage). Traps were left in the cage for 3.5 days then removed and numbers of males and females in each trap were recorded.

Results are give in Table 3. These include total flies trapped during the final 3 days of the tests. In this table each cell total for bait or bait plus dye represents the sum of two cells. In the early tests (1 and 2) the survival rate for flies was very low due to ant and spider predation on the emerging adults and the flies had many alternative food sources from the pest infestations on the trees. Survival rates were much higher in tests 3–7 but cool weather and rain storms slowed the feeding and trapping rate during some of the tests. Statistics were calculated for the effects of the dye as an Analysis of Variance with either the numbers of the flies recaptured or as the percentage of flies recaptured as a dependent variable. In either case the effect of the dye was highly significant.

EXAMPLE 1

RESPONSE OF THE MEXICAN FRUIT FLY HYDROLYZED PROTEIN BAITS

The standard malathion-bait used to control fruit flies world-wide is composed of 20% (AI) malathion and 80% NuLure (formerly PIB-7, hydrolyzed protein from corn steep). The malathion is the toxicant and NuLure is the food attractant. This formulation is applied by air and when the flies are attracted to it, they are killed by contact or by ingestion of the formulation. However, we have found in our laboratory that Mexican fruitflies do not readily ingest NuLure. Given a more palatable choice, flies consume very little NuLure. Table 1 shows that NuLure presented to flies, either undiluted or in a 60% formulation with incremental amounts of fructose added, and at the same time Mazoferm (hydrolyzed protein from corn steep) is presented, the flies prefer to consume Mazoferm with or without fructose as a feeding stimulant.

TABLE 1

Food consumption (mg) by female Mexican fruit flies of two different protein hydrolysates.

| | Mean/80 females | |
| --- | --- | --- |
| % Fructose | Mazoferm | NuLure |
| 0 | 179.4 ± 15.6 | 27.0 ± 06.3 |
| 4 | 173.5 ± 18.8 | 66.5 ± 20.5 |
| 12 | 281.7 ± 22.7 | 104.5 ± 09.6 |
| 20 | 279.4 ± 21.7 | 98.5 ± 10.9 |

EXAMPLE 2

Using Mazoferm as the bait, we conducted a test with phloxine-B at concentrations of 0 Mazoferm check), 0.25, 0.5, 1.0, 2.0 and 4.0%. The formulation consisting of 70% Mazoferm, 20% fructose as a feeding stimulant, 0.1% SM-9 (adjuvant) and water. Food was presented to flies for 24 h and then the cages taken out and flies exposed to sunlight for 4 h (from 0900 to 1300 h CST). Table 2 shows that the effectiveness of the dye is dosage dependent and light-exposure dependent. There was no significant difference in food consumption among groups of flies at the various concentrations. Thus indicating that at these concentrations flies are not deterred form feeding by the dye.

TABLE 2

Effectiveness of phloxine-B in killing female Mexican fruit flies after feeding on the material and exposed to sunlight for four hours.

| % Concentration | Mean percentage mortality | |
| --- | --- | --- |
| | 2 hours | 4 hours |
| 0.00 | 4.0 ± 2.9 | 6.0 ± 3.7 |
| 0.25 | 28.0 ± 3.0 | 79.0 ± 7.0 |
| 0.50 | 38.0 ± 7.2 | 93.0 ± 2.0 |
| 1.00 | 74.0 ± 8.1 | 98.0 ± 1.2 |
| 2.00 | 90.0 ± 3.5 | 99.0 ± 1.0 |
| 4.00 | 100.0 ± 0.0 | 100.0 ± 0.0 |

The Mexican fruit fly normally requires 10–15 days to mature. Normally adults feed continuously on protein sources from day 5 through the rest of their lives. We were able to cause highly significant mortality reduction in fly survival (based on trap sampling) averaging over 70% in 5 days.

TABLE 3

Recapture of flies in Bait or Bait + Dye Cages

| Test | Captured Bait Only Number | % | Captured Bait & Dye Number | % | Total Flies Captured |
| --- | --- | --- | --- | --- | --- |
| 1 | 163 | 69.3 | 72 | 30.7 | 235 |
| 2 | 174 | 80.5 | 42 | 19.5 | 216 |
| 3 | 609 | 70.1 | 260 | 29.9 | 869 |
| 4 | 2,064 | 84.8 | 280 | 15.2 | 2,344 |
| 5 | 879 | 77.9 | 230 | 22.1 | 1,127 |
| 6 | 355 | 56.7 | 256 | 43.3 | 591 |
| 7 | 1,184 | 77.4 | 317 | 22.7 | 1,530 |

TABLE 4

Analysis of Variance results for effects of cage, dye treatment, on percentage of flies recaptured in 7 tests.

| Source | DF | Mean Square | F-Ratio | Prob. |
| --- | --- | --- | --- | --- |
| Cage | 3 | 269.52 | 3.37 | 0.04 |
| Treatment | 1 | 4,043.55 | 50.59 | <0001 |
| Error | 23 | 79.92 | | |

TABLE 5

Analysis of Variance results for effects of cage, dye treatment, and test on numbers of flies recaptured in 7 tests.

| Source | DF | Mean Square | F-Ratio | Prob. |
| --- | --- | --- | --- | --- |
| Cage | 3 | 34,259.67 | 0.81 | 0.51 |
| Test | 6 | 145,274.24 | 3.45 | 0.02 |
| Treatment | 1 | 600,625.29 | 14.26 | <0.005 |
| Error | 17 | 42,124.57 | | |

We have also determined through testing, that the "knock down" effect for flies that have been fed on low dosages of the composition of the present invention (less than 0.5%) can be greatly increased by addition of certain adjuvants such as SM-9 (secondary alcohol ethoxylate) that enhance the absorption of herbicides and insecticides in delivery systems.

The ratio and absolute amounts of the photodye and enzymatic hydrolyzed protein in commercial formulations may vary and may be readily predetermined by the practitioner skilled in the art by routine testing. It will be recognized that the photodye should be employed in an amount effective to result in a significant growth inhibition or mortality rate of a test group of the target insect as compared to an untreated group. Furthermore, the amount of enzyme hydrolyzed protein employed should be effective to attract the target insect. The actual effective amounts of the photodye and enzyme hydrolyzed protein may vary with environmental conditions such as temperature, humidity and wind; the type of vehicle or carrier employed; application protocol and state of target insect development.

The present invention relates to an insecticidal composition which includes at least one photoactive dye selected form a group of photoactive dyes having a known efficacy when used in the composition for a specific targeted species of insects. The composition further includes at least one attractant compound (bait) and/or an insect feeding stimulant to attract the targeted species of insect so that the targeted insect will consume the composition. Finally, the composition includes at least one adjuvant selected form a group of adjuvants, wherein the selected adjuvant has a known effect in altering the toxicity of the selected photoactive dye once consumed by the targeted insect. Accordingly, use of the selected adjuvant or adjuvants in the composition enables control and manipulation of the time of kill and rate of kill of the targeted insect species.

Through a series of detailed and exhaustive experimental tests, a large number of compounds in an array of chemical groups has been found to have phototoxic effects on specific insects and the toxic activity of these dyes consumed by the targeted insect has been effectively regulated to control the insecticidal efficacy through the use of selected adjuvants. The following are examples of photoactive dyes which have been found to exhibit phototoxic activity in specific insects when used with one or more selected adjuvants:

Azure A
Azure B
Methylene Blue
New Methylene B1 N
Toluidine Blue
Methylene Green
Thionin
Rhodamine B
Thioflavine T
Eosine Y
Erythrosine B
Phloxine B
Pyronine Y
Rhodamine 6 G
Rose Bengal
D&C Orange 5
Pyronine B
Neutral Red
Safranin O
Auramine O
Alizarin Red S Included in this list are several dyes which are used in food, drugs and cosmetics, or as dyes for cloth, leather, wool, cotton, and the like. These dyes have been approved by the FDA for use in food, drug, and cosmetics.

Specifically, the dyes Eosine Y, Erythrosine B, D&C Orange 5, Safranin O, Thioflavine T, and Auramine O were found to exhibit far superior efficacy as insecticides in comparison with phloxine B, when used with an optimal adjuvant. Without the specific adjuvants, certain of these dyes have little or no toxic activity as insecticides. In fact, Erythrosine B has been cited in scientific literature as being superior to phloxine B for use as a phototoxic insecticidal dye.

Different embodiments of the composition, comprising at least one of the photoactive dyes, an attractant and/or feeding stimulant, and at least one adjuvant, have been tested on a number of different insect species in different insect groups. The following is a list of insects which have been killed during testing the various embodiments of the composition.

| | |
|---|---|
| Mediterranean Fruit Fly | Boll Weevil |
| Mexican Fruit Fly | Citrus Weevil |
| Oriental Fruit Fly | Soybean Looper |
| Melon Fruit Fly | Diamond Back Moth |
| Malaysian Fruit Fly | Imported Fire Ant |
| Caribbean Fruit Fly | Grasshopper |
| Cabbage Looper | Fern Caterpillar |
| Apple Maggot | Mosquito Larvae |
| Codling Moth | Fall Army Worm |
| Pink Boll Worm | Beet Army Worm |
| Mexican Rice Boll Worm | Colorado Potato Beetle |
| Corn Ear Worm | Cockroach |
| Tobacco Bud Worm | House Fly |
| Face Fly | Corn Root Worm |

In each of the tests on the above insects, the previously identified photoactive dyes were tested in combination with one or more adjuvants selected from the following group:

| | |
|---|---|
| SM-9 Standard | Tergitol S-9 |
| Dyne-Amic | Solvaid |
| Sylgard | VapoGard |
| Century | Tergitol S-3 |
| Latron B-1956 | Citrufilm |
| Latron CS-7 | Latron AG-98 |
| Tween 20 | Micro |
| Tween 60 | Silwet L-77 |
| Tween 80 | Triton X-100 |
| Hasten | NuFilm 17 |
| Kinetic | NuFilm P |

Among the preferred adjuvants useful in this invention are the following:

SM-9, an alkyloxypolyethyleneoxyethanol, previously described.

Tween 60 is a well known ingredient used as an emulsifier and stabilizer in the food industry. It is known chemically as polyoxyethylene-sorbitan monostearate. Tween 60 is more fully described in Food Additives Handbook (editor Lewis) published by Van Nostand Reinhold, New York.

While Tween 60 is a preferred adjuvant, other members of the Tween series of adjuvants would be operative.

The following is a summary of experiments conducted to determine the effect of selected adjuvants on the phototoxicity of certain dyes on the female Mexican fruit fly (*Anastrepha ludens*), house fly larvae in manure piles, and fire ants.

EXPERIMENT 1

In this experiment, the effect of selected adjuvants on the phototoxicity of certain dyes on female Mexican fruit flies was determined. The levels of activities of various dye/adjuvant combinations are shown in Table 6 and 7. The numbers shown in the following tables are percentage of flies killed after 24 hours of feeding and then exposure to sunlight until the most toxic combination in the series reached maximum kill (up to 4 hours). Light intensity was variable among tests, but in the majority of the tests, at least one combination had a greater than 50% mortality.

TABLE 6

Effect of Selected Adjuvants on the Phototoxicity of Certain Dyes on Female Mexican Fruit Fly, *Anastrepha ludens*

| Adjuvants (1%) | % Mortality in the First Spike of Phototoxicity Phloxine B 0.0382% | | | | | Rose bengal 0.03% |
|---|---|---|---|---|---|---|
| Control | — | — | 2c | — | — | 0b |
| Check | 0b | 0c | 1c | 0b | 4d | 0b |
| SM-9 Standard | 2b | 63b | 14b | 70a | 64b | 7b |
| Dyne-Amic | | 28c | | | | |
| Sylgard | | 94a | | | | |
| Century | | 67b | | | | |
| Latron B-1956 | | 5c | | | | |
| Latron CS-7 | | 2c | | | | |
| Tween 20 | | | 20b | | | |
| Tween 60 | | | 31a | | | |
| Tween 80 | | | 15b | | | |
| Hasten | | | | 9b | | 0b |
| Kinetic | 67a | | | | | 52a |
| Tergitol S-9 | | | | 17b | | 7b |
| Solvaid | | | | 8b | | |
| VapoGard | | | | 16b | | |
| Tergitol S-3 | | | | | | |
| Citrofilm | | | | | 86a | |
| Latron AG-98 | | | | | 83a | |
| Micro | 5b | | | | | |
| Silwet L-77 | 14b | | | | | |
| Triton X-100 | 4b | | | | | |
| NuFilm 17 | | | | | | 10d |
| NuFilm P | | | | | | 38c |

All adjuvants and dyes were tested in a medium of Mazoferm-Invertose-Water which was fed to flies. Controls contained no adjuvants or dyes; checks contained appropriate dyes but no adjuvants. Means within columns followed by the same letter are not significantly different at p = 0.05 (Fisher's Protected LSD).

TABLE 7

Effect of Selected Adjuvants on the Phototoxicity of Certain Dyes on Female Mexican Fruit Fly, *Anastrepha ludens*

| Adjuvants (1%) | % Mortality in the First Spike of Phototoxicity | | | | | |
|---|---|---|---|---|---|---|
| | Erythrosin 0.025% | Methylene blue 0.0315% | Azure B 0.03% | Rhodamine 6G 0.023% | | Thioflavine T 0.045% |
| Control | 0c | 0d | 3b | 2b | 0d | 0b |
| Check | 0c | 91b | 2b | 5b | 0d | 4b |
| SM-9 Standard | 24a | 98a | 41a | 18a | 56b | 67a |
| Dyne-Amic | | | | | | |
| Sylgard | | 43a | | | | |
| Century | | | | | | |
| Latron B-1956 | | | | | | |
| Latron CS-7 | | | | | | |
| Tween 20 | | | | | | |
| Tween 60 | | | | 4b | | |
| Tween 80 | | | | | | |
| Hasten | 0c | 72c | | | 0d | |
| Kinetic | 37a | 96a | | 10b | 46c | |
| Tergitol S-9 | 16b | 99a | | | 80a | |
| Solvaid | | | | | | |
| VapoGard | | | | | | 8b |
| Tergitol S-3 | | 42a | 8b | | | 61a |
| Citrufilm | | | | | | |

TABLE 7-continued

Effect of Selected Adjuvants on the Phototoxicity of Certain Dyes on Female Mexican Fruit Fly, *Anastrepha ludens*

| Adjuvants (1%) | % Mortality in the First Spike of Phototoxicity | | | | |
|---|---|---|---|---|---|
| | Erythrosin 0.025% | Methylene blue 0.0315% | Azure B 0.03% | Rhodamine 6G 0.023% | Thioflavine T 0.045% |
| Latron AG-98 | | | 45a | | |
| Micro | | | | | |
| Silwet L-77 | | | | | |
| Triton X-100 | | | | | |
| NuFilm 17 | | | | | |
| NuFilm P | | | | | |

All adjuvant and dyes were tested in a medium of Mazoferm-Invertose-Water which was fed to flies. Controls contained no adjuvants or dyes; checks contained appropriate dyes but not adjuvants. Means within columns followed by the same letter are not significantly different at p = 0.05 (Fisher's Protected LSD).

Table 8 shows a list and the characteristics all dyes tested and having some photodynamic toxicity to fruit flies at less than 0.1% concentration. The majority of these dyes have not previously been reported to have any photodynamic toxicity to insects and several have been tested as set forth in previous publications (without adjuvants) and no toxicity was reported. This experiment has proven that the use of selected adjuvants in combination with at least one photoactive dye results in an internal process in the insect which gives a toxic effect.

toxicity from the control (bait alone) but the addition of 1% of at least one of the adjuvants resulted in highly significant mortality. The activity of the adjuvants appears to be maximal in enhancing the toxicity at about 1% volume. Enhancing the solubility of the dye in the bait is, however, only a minor function of the adjuvant, as the solubility appears to be maximized at about 0.1% adjuvant by volume. Further, the toxicity of the compounds is unrelated or only weakly related to the dye solubility in the aqueous bait. Referring to Table 8, methylene blue with a solubility of 50 mg/mlH$_2$O has a similar LC 50 (concentration to kill 50% of test population) to phloxine B with a solubility of 90 mg/ml H$_2$O and Toluidine Blue at 10 mg/mlH$_2$O.

Different adjuvants had drastically different effects on rate of mortality with the same dye, even in cases with very similar chemical properties of the adjuvants. Tween 60 (Table 6) was significantly more effective than Tween 80 and NuFilm P was significantly more effective than NuFilm 17 with phloxine B.

It was observed that the passage of dyes into the hemolymph of the insect was highly dependent on the individual dyes and on individual adjuvants. The appearance of dye in the hemolymph (Table 8) was not observed to be directly related to mortality effects on the insect. Rhodamine B, for example, dyed the body and legs of the insect bright red when used with SM-9 adjuvant, but was only about 30% as toxic to the insect (LC 50=0.09% for Rhodamine B versus 0.030% for phloxine B). These effects further support our contention that the adjuvants have activity that enhances the photodynamic action of the dyes inside the insects and this activity differs among dyes and adjuvants, but is not due to general solubility mechanisms.

The time delay from exposure to light to the onset of mortality was dependent on an interaction of specific char-

TABLE 8

Dyes With Phototoxic Action on the Mexican Fruit Fly, *Anastrepha ludens* Loew

| Dye Name | CI No. | Group/Sub | Charge | Mol. Wt. | Absorb. Max | LC$_{50}$(%) | Sol. H$_2$O (mg/ml) | Common Use for Dye |
|---|---|---|---|---|---|---|---|---|
| New Methylene B1 N | 52030 | Thiazine | Cationic | 416.0 | 630 | 0.0174 | 40 | Silk, wood, paper, leather |
| Azure A | 52005 | Thiazine | Cationic | 291.8 | 633 | | 40 | Histology |
| Azure B* | 52010 | Thiazine | Cationic | 305.8 | 648 | | 50 | Histology |
| Methylene blue | 52015 | Thiazine | Cationic | 373.0 | 661 | 0.0315 | 50 | Antiseptic, histology |
| Toluidine blue | 52040 | Thiazine | Cationic | 305.8 | 626 | 0.3004 | 10 | Histology |
| Methylene green* | 52020 | Thiazine | Cationic | 433.0 | 657 | 0.2114 | 30 | Histology |
| Thionin | 52000 | Thiazine | Cationic | 387.3 | 598 | | 30 | Histology |
| Brilliant Cresylblue* | 51010 | Oxazine | Cationic | 386.0 | 622 | 0.0389 | — | Histology |
| Rhodamine B | 45170 | Rhodamine | Cationic | 479.0 | 543 | 0.0982 | 30 | Cotton, wool |
| Thioflavine T | 49005 | Thiazole | Cationic | 318.9 | 412 | 0.0303 | 20 | Silk, wool, flylon, acetate |
| Eosine Y | 45380 | Xanthene | Anionic | 691.9 | 514 | | 40 | Histology |
| Erythrosine B | 45430 | Xanthene | Anionic | 879.9 | 525 | 0.0141 | 20 | Food |
| Phloxine B | 45410 | Xanthene | Anionic | 829.7 | 548 | 0.0382 | 90 | Food, cosmetic |
| Pyronine Y | 45005 | Xanthene | Cationic | 302.8 | 548 | 0.2495 | 30 | Histology |
| Rhodamine 6G* | 45160 | Xanthene | Cationic | 479.0 | 524 | 0.0230 | 20 | Printing |
| Rose bengal | 45440 | Xanthene | Anionic | 1017.7 | 548 | | 100 | Food, cosmetics |
| D & C Orange 5 | 45370A | Xanthene | Anionic | 490.1 | 450 | | 0.3 | Cosmetics |
| Pyronine B | 45010 | Xanthene | Cationic | 1042.3 | 553 | | 20 | Photography, histology |
| Neutral red | 50040 | Azine | Cationic | 288.8 | 540 | | 40 | Supravital staining |
| Safranin O | 50240 | Azine | Cationic | 350.9 | 530 | 0.0092 | 50 | Cotton, paper, leather |
| Auramine O | 4100 | Diphenylmethane | Cationic | 303.8 | 432 | | 10 | Cotton, silk, wool, leather |
| Alizarin Red S | 58005 | Anthraquinone | Anionic | 360.3 | 556 | | 20 | Indicator, histology |

Dyes were fed to flies in a bait formulation of 70% Mazoferm - 20% Invertose - 1% SM9-Water
These dyes colored the whole body of flies, except wings.

Figure 2:
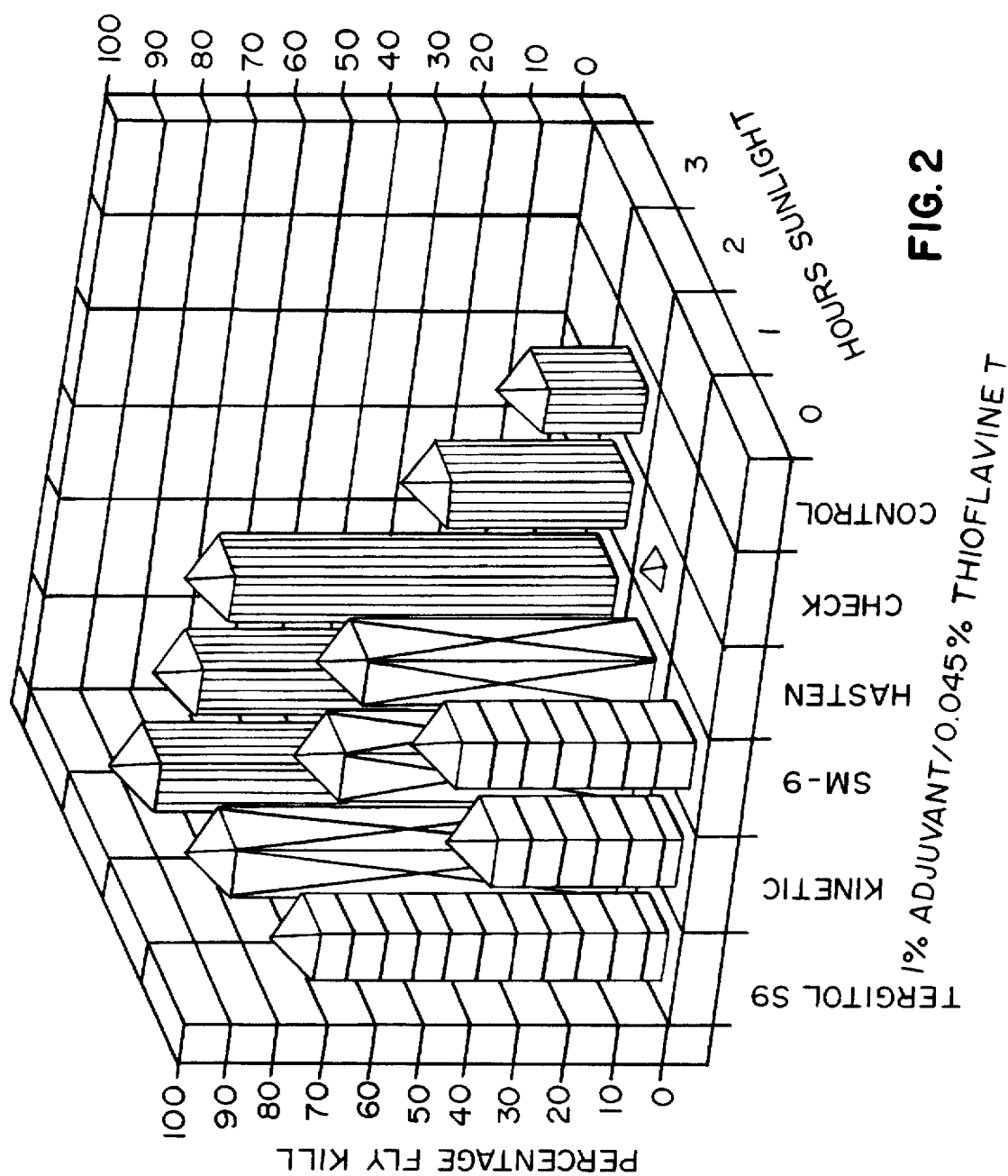

For a major portion of the dyes at low concentrations (<0.3%), the check dye alone did not significantly differ in acteristics of the dye and the adjuvant. This is illustrated in FIGS. 1 and 2.

Thioflavine T at 0.045% concentration (the estimated LC 50), with the optimal adjuvant, killed the majority of the flies before being exposed to light, but had no effect with Hasten or without the adjuvant until after two hours exposure to light. Erythrosine B at the 0.025% concentration (also the LC 50) caused no mortality with any adjuvant until after two hours exposure to light, but killed most of the insects (and was more effective than Thioflavine T) with the effective adjuvants during the 2–3 hour time period. With no adjuvant, or with Hasten, the Erythrosine B caused no mortality.

The data, in Tables 6 and 7, comparing check (dye and bait with no adjuvant) and the best adjuvants (dye, bait, adjuvant combination) indicates that greater than 90% mortality can frequently be induced at dye concentrations with adjuvant at the same concentrations that cause no significant mortality in trials without adjuvants.

In addition, the data in Table 9 (below) demonstrates the cumulative mortality rates per hour for a series of concentrations of phloxine B without adjuvant, and a more than 10-fold decrease in dye concentration with adjuvant. From these observations, it is concluded that the use of adjuvants (1%) allows reduction in dye concentrations by factors of 10 to 50 times of concentration in comparison with formulations without adjuvants. Thus, this experiment has proved the existence of an otherwise unexpected relationship between toxic dyes and a series of adjuvants. The dye and adjuvant combination causes an increased or decreased toxicity depending upon the specific combination of dyes and adjuvants. Further, the increase or decrease of toxicity is not based entirely on solubility considerations of a linear nature.

TABLE 9

Hourly cumulative mortality rates of daylight-exposed Mexican fruit flies that were fed baits with no dye, with 0.038% dye with adjuvant and with increasing concentrations of dye without adjuvants.

| Phloxine B | Percentage Mortality | | | |
|---|---|---|---|---|
| | 1 hour | 2 hours | 3 hours | 4 hours |
| Concentration | | | | |
| 0 (control) | 0 | 0 | 0 | 0 |
| 0.038% | 0 | 0 | 0 | 4 |
| 0.251% | 0 | 0 | 2 | 3 |
| 0.5% | 0 | 24 | 53 | 61 |
| 0.038%+ SM9 (Adj) | 4 | 65 | 92 | 98 |

EXPERIMENT 2

This experiment was conducted in order to determine the efficacy of a dye, bait, and adjuvant combination as a phototoxic insecticide for fly larvae. Three different formulas were tested in cow manure piles to determine their toxic efficacy. A first formula contained 4% phloxine B mixed with deionized water. The second formula contained 3% phloxine B, 1% uranine and deionized water. The third formula was comprised of 3% phloxine B, 1% uranine, and 2% adjuvant. The kill rate was measured over a period of one week at 2 to 3 day intervals. The kill rate results are shown in Table 10.

TABLE 10

Purpose: Determine the efficacy of photoactive dyes on fly larvae in manure piles Formula 262-1  Contains 4% phloxine B
Formula 262-2  Contains 3% phloxine B; 1% uranine
Formula 263-3  Contains 3% phloxine B; 1% uranine; 2% adjuvant
The balance of the formula is deionized water
Product applied at the rate of 2 ounces per 100 square feet of manure pile
Initial Application: 5/18/95
Kill Rate Results:

| Formula | 5/19/95 | 5/21/95 | 5/23/95 | 5/26/95 |
|---|---|---|---|---|
| 262-1 | 10% | 20% | 40% | 60% |
| 262-2 | 10% | 40% | 50% | 80% |
| 262-3 | 20% | 80% | 95% | 95% |

The results of this experiment indicate that the combination of phloxine B and uranine produce better and faster kill rates than phloxine B alone. The addition of the adjuvant accelerates the kill rate, achieving superior results in comparison with phloxine B alone or phloxine B with uranine.

EXPERIMENT 3

This experiment was conducted in order to determine the toxic effect of various formulations of a phototoxic composition, with and without an adjuvant, on fire ants.

Three different formulas were tested on fire ants to measure their kill rates. The first formula contained 4% phloxine B, 1% peanut oil, 1% corn oil, and corn cob grits making up the difference to 100%. The second formula contained 3% phloxine B, 1% uranine, 1% peanut oil, 1% corn oil and corn cob grits to 100% The third formula was comprised of 3% phloxine B, 1% uranine, and 2% adjuvant, along with 1% peanut oil, 1% corn oil, and corn cob grits to make up the different to 100%. The kill rate was measured over a period of one week at intervals of every two to three days. The kill rate results are shown in Table 11 (below).

TABLE 11

Purpose: Determine the efficacy of various formulations that contain the following combination of active ingredients.

238A - 4% phloxine B
238B - 3% phloxine B; 1% uranine
238C - 3% phloxine B; 1% uranine; 2% adjuvant The balance of the formulations contains 1% peanut Oil, 1% corn oil and corn cob grits making up the difference to 100%.
Initial Application - 8/2/94 TestSite; Bluffton, South Carolina
Product applied at the rate of 1 ounce per 5 square feet of ant hill mound.
Kill Rate Results:

| Formula | 8/3/94 | 8/5/94 | 8/7/94 | 8/10/94 |
|---|---|---|---|---|
| 238A | 10% | 20% | 40% | 60% |
| 238B | 10% | 30% | 60% | 100% |
| 238C | 20% | 80% | 100% | 100% |

The results indicate that the combination of phloxine B and uranine exhibit better results than phloxine B by itself. The addition of the adjuvant greatly enhances the kill rate of the combination of phloxine B and uranine.

The present invention contemplates the use of various attractant compounds and/or feeding stimulant compounds. In experiment 1 as set forth above, the adjuvants and dyes were tested in a medium of Mazoferm-Invertose-Water which was fed to the female Mexican fruit fly. In experiment 2, cow manure was used as an attractant for fly larvae. In experiment 3, a formulation of peanut oil, corn oil, and corn cob grits was used as an attractant for fire ants.

Preferred photoactive dyes used by the inventors are phloxine B or phloxine B plus uranine in combination on the Mexican fruitfly. A toxic concentration of phloxine B in sugar water could be less than 1%. The inventors have tested torula yeast, casein hydrolyzate, yeast hydrolyzate and Mazoferm, a hydrolyzed corn protein.

Laboratory and field tests have been carried out. The tests were made in deionized water: 2.22% torula yeast (equivalent amount in a torula yeast tablet; 50% protein), 2.22% casein hydrolyzate (≈87% protein) 2.22% yeast hydrolyzate (≈50% protein), 10% Mazoferm 802 (≈22% protein), and 10% NuLure (≈22% protein). In addition, 0.01% Triton X-100 was added to break water surface tension. The pH of all the suspensions was adjusted to eight with dibasic sodium phosphate, and in addition, potassium hydroxide in the case of Mazoferm and NuLure which had received 4% dibasic sodium phosphate. These concentrations were chosen based on conventional use of torula yeast and NuLure in the field. The field test was conducted with released irradiated flies in a citrus orchard comprising 'Rio Red' grapefruit planted in 1990.

Laboratory results (FIG. 3) indicate that the hydrolyzed proteins of casein, yeast, Mazoferm, and NuLure were significantly more attractive than the unhydrolyzed torula yeast or water. This, indicates that any of these could be used as attractive sources for *A. ludens*. However, when this same test was conducted in the field, torula yeast, yeast hydrolyzate, casein hydrolyzate, and Mazoferm were significantly more attractive than water or NuLure (FIG. 4). The surprise in the field test was that NuLure, which had been significantly more attractive than torula yeast or water in the previous test was not now attractive.

Figure 3:
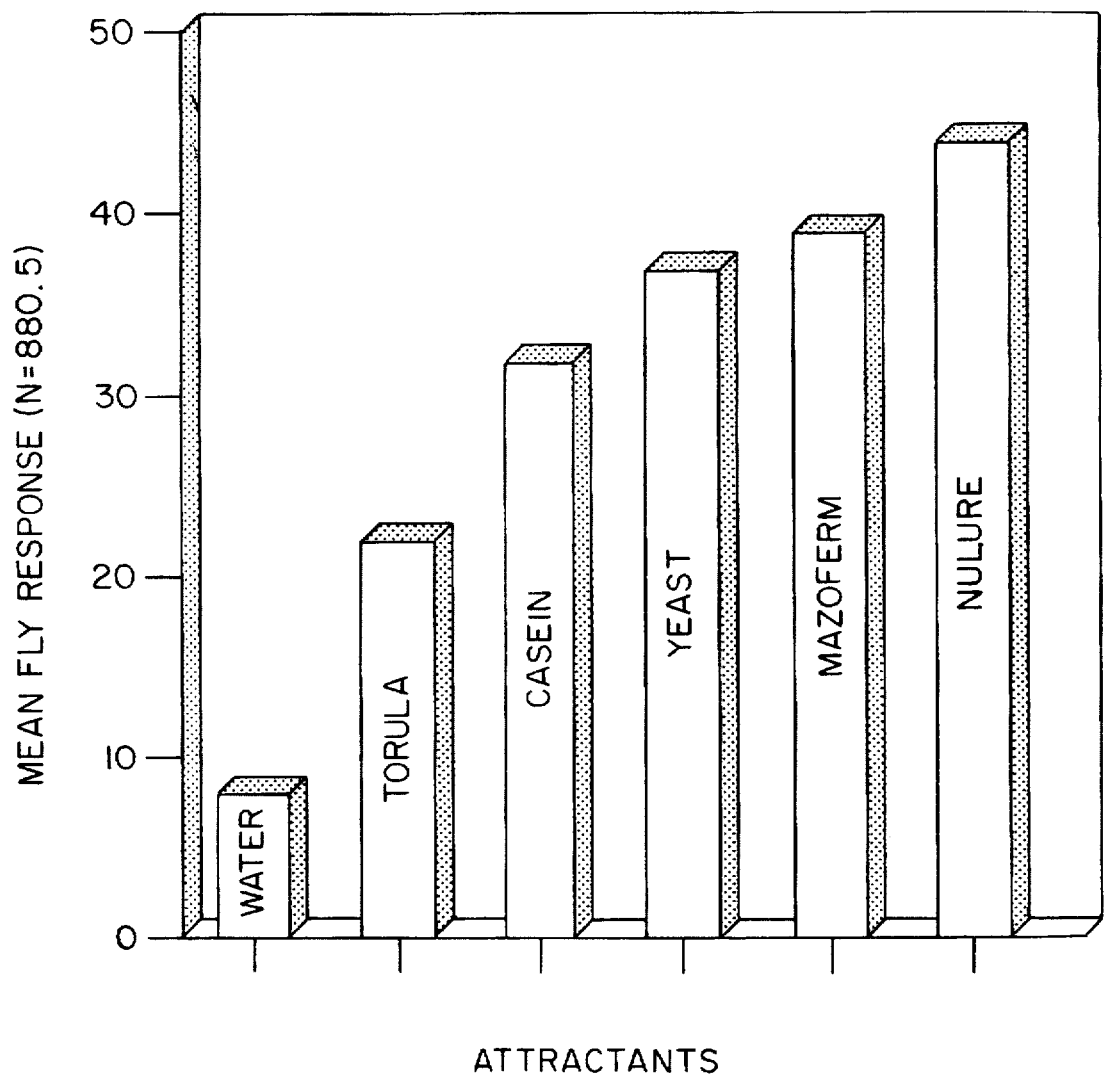
FIG. 3 shows the response in the laboratory of A. ludens to various protein hydrolyzates.
Figure 4:
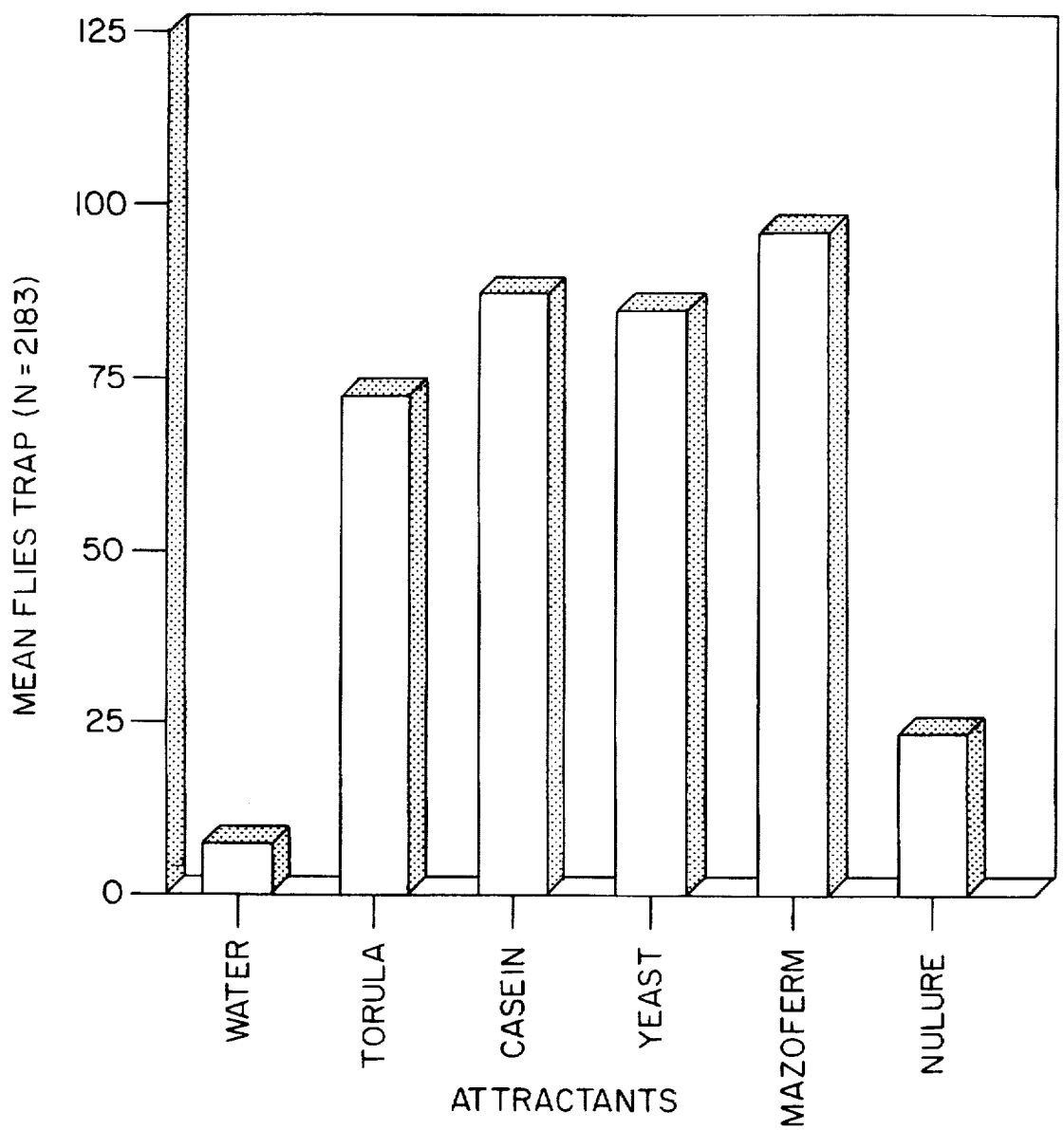
FIG. 4 shows the response in the field of A. ludens to various protein hydrolyzates.

FIG. 3 is the response in the laboratory of *A. ludens* to water homogenates of 2.22% torula yeast, 2.22% casein hydrolyzate, 2.22% yeast hydrolyzate, 10% Mazoferm 802, and 10% NuLure. All attractants were adjusted to pH 8.

FIG. 4 is the response of *A. ludens* to water homogenates of 2.22% torula yeast, 2.22% casein hydrolyzate, 2.22% yeast hydrolyzate, 10% Mazoferm 802, and 10% NuLure in the field. All attractants were adjusted to pH 8 and placed in plastic McPhail type traps.

The inventors tested the relative attractiveness of low (10%), medium (40%), and high (70%) concentrations of Mazoferm against NuLure in the laboratory. The 70% concentration approached that of NuLure (≈80%) used in aerial ultra low-volume applications. They wanted to determine if increasing concentrations of hydrolyzed protein would enhance attraction to flies. Results (FIG. 3) of the tests indicate that higher concentrations of Mazoferm enhance attraction but NuLure does not. The attraction profile of NuLure indicates a slight descending order whereas that of Mazoferm is ascending. The attraction of Mazoferm and NuLure at a concentration of 10% is about equal but at concentrations of 40 and 70%, Mazoferm is significantly more attractive than NuLure. It clearly appears that Mazoferm would be the ingredient of choice among these two hydrolyzed proteins and that a medium to high concentration of Mazoferm is preferred over lower concentrations.

The previous tests indicate that any one of the attractants could be used to lure flies in ultralow-volume spray applications but because torula yeast, yeast hydrolyzate, and casein are costly, the best candidates are Mazoferm and NuLure. The former three are produced for human consumption and for that reason should be considered safe. The latter two are corn products and are used in animal food mixes because of their high protein content. Mazoferm is produced in the wet milling process in which the corn is soaked in a warm dilute sulfurous acid solution, then, the extract undergoes a mild lactic acid fermentation from naturally occurring microorganisms. Whereas NuLure is the product of corn gluten meal hydrolyzed with strong sulfuric acid. The difference in the method of hydrolysis eventually differentiates few characteristics among the products. The approximate typical (information provided by the producers) composition (%) of Mazoferm:NuLure is protein 22:22 (with very similar amino acid profiles differing only in the presence of cystine and tyrosine in Mazoferm), sugars 6:14, fat 0.2:2, salt 0.15:10.4, and solids 49:48, and with pH 4:3.7, respectively. However, NuLure has been the standard in ultralow-volume aerial spray applications and for that reason further evaluation of the two products was necessary.

CONSUMPTION: NO CHOICE AND CHOICE TESTS

These tests (Table 12) were set up to determine the acceptance of Mazoferm or NuLure based on the consumption of the products by adult Mexican fruit flies. In the no choice tests, the consumption of each of the products was measured against the consumption of fructose, a simple sugar that insects quickly utilize and was found to be highly accepted by the house fly, *Musca domestica* L. In a separate study, it was found that fructose and sucrose promoted maximum survival of adult Mexican fruit flies as compared to other sugars. The treatment for each of the hydrolyzates was 0, 4, 8, 12, 16, 20, and 24% fructose in a 60% Mazoferm- or NuLure-base compared to the consumption of fructose crystals. Fructose was added on a weight to volume basis using deionized water as the diluent and 0.01% Triton X-100 (SIGMA Chemical Company, St. Louis, Mo.) as an aid in the emulsification of the products. Consumption of food was measured by weighing a 16 mm plastic dish, a screen which served as a walking platform for flies, and the formulated food before and after exposure to flies. Each of the dishes was placed next to the screen inside the cage; a similarly prepared dish was placed on the outside of the screen tangential to the dish inside the cage. Net consumption of food by flies in replicated groups was corrected to changes occurring in the control (outside dish). In the no choice tests we used groups of 40 flies (20 females and 20 males) per replicate. Thus, the results (Table 12) for the no-choice tests indicate that for Mazoferm increasing amounts of fructose stimulate greater consumption of food. Consumption at the 16% or higher concentrations of fructose was significantly higher than that of fructose alone. This indicates that the flies found the food more palatable with the addition of fructose as compared to no fructose. However, the addition of 4% fructose to Mazoferm does not significantly increase food consumption over the base formulation. Thus, whatever factors the sweetness of fructose need to overcome in Mazoferm at 4%, the amount is not sufficient to do so. In contrast, a 4% addition of fructose to NuLure significantly increased consumption. However, increased consumption flattens at a concentration of 16% fructose but at no concentration did consumption exceed that of fructose alone. The data for NuLure tends to suggest, as compared to Mazoferm, that something in the NuLure-base formulation limits feeding.

TABLE 12

Consumption of Fructose in a 60% Mazoferm 802 or NuLure Aqueous Suspension by *A. ludens*, in 24 h, in Independent No-choice Tests

| % Concn fructose | Mean[a] (±SEM) Consumption (mg) | |
|---|---|---|
| | Mazoferm | NuLure |
| 0 | 79.6 ± 8.7 | 47.7 ± 3.1 |
| 4 | 87.7 ± 1.9 | 78.0 ± 4.0 |
| 8 | 111.5 ± 7.4 | 97.6 ± 6.7 |
| 12 | 126.8 ± 4.3 | 81.5 ± 3.1 |
| 16 | 137.6 ± 5.2 | 101.2 ± 5.7 |
| 20 | 152.6 ± 10.0 | 110.3 ± 5.4 |
| 24 | 210.1 ± 12.0 | 114.3 ± 12.4 |
| 100 (fructose only) | 109.7 ± 7.1 | 156.6 ± 6.9 |

[a]Mean of five replicates, 40 flies per replicate

In the choice tests (Table 13), we took the same approach as in the no choice tests of placing dishes inside and outside the screen of each test cage. However, in this test, the flies had a choice of consuming either a 60% Mazoferm- or 60% NuLure-base formulation that contained 0, 4, 12, and 20% fructose. We used 80 females per replicate. The results of this test (Table 13) clearly show that flies significantly preferred a Mazoferm-base formulation with or without fructose to that of NuLure with or without fructose. Flies consumed 6.9 times more Mazoferm without fructose as that of NuLure without fructose. Again, we see that 4% of fructose in the Mazoferm formulation does not increase consumption significantly over that without fructose but there is a significant increase with the addition of 12 or 20% fructose. However, there is no significant difference among these two concentrations. Inasmuch as some consumption of NuLure took place, perhaps sensorial sensitivity became attenuated.

As a follow-up to the previous test, we set up a test to determine the food quality of Mazoferm and NuLure measured by the time that it took 50% of flies to die ($LT_{50}$). The idea was that the nutritional quality of the food should be reflected in the adult longevity of flies. The treatments for this test were a 60% Mazoferm- or NuLure-base formulation and the addition of 12% fructose to each as a feeding stimulant. We used 80 females per replicate times five replicates per treatment. Deaths were recorded three times a day from the time they were given the formulation to the time 50% of them died. Old food was removed and fresh food was provided every other day (except week ends). The results (Table 14) of this test indicate that the Mazoferm-base formulation has significantly better nutritional qualities than those of the NuLure-base formulation. Inasmuch as basic survival of flies depends on assimilative carbohydrates, the data suggests that Mazoferm has more assimilative carbohydrates than NuLure. This inference is attested by the similarity in survival of flies given Mazoferm or NuLure with 12% fructose. Here, the amount of fructose provided, apparently superseded the differences in assimilative carbohydrates among Mazoferm and NuLure.

TABLE 13

Consumption of Fructose in a 60% Mazoferm of NuLure Aqueous Suspensions by *A. ludens* in 24 h, Choice Tests

| % Concn fructose | Mean[a] (±SEM) Consumption (mg) | |
|---|---|---|
| | Mazoferm | NuLure |
| 0 | 170.8 ± 9.7 | 24.7 ± 4.1 |
| 4 | 183.1 ± 13.4 | 48.5 ± 11.5 |
| 12 | 280.7 ± 4.3 | 91.5 ± 14.4 |
| 20 | 280.6 ± 13.6 | 110.3 ± 5.4 |

[a]Mean of five replicates, 80 females per replicate

TABLE 14

Time Lapsed for 50% Female *A. ludens* to Die When Fed Only Indicated Diets Plus Water

| 60% ingredient | Mean[a] (±SEM) $LT_{50}$ Death(h) |
|---|---|
| Mazoferm 802 | 106.0 ± 0.0 |
| NuLure | 58.0 ± 0.0 |
| Mazoferm ± 12% fructose | 236.2 ± 5.3 |
| NuLure ± 12% fructose | 237.8 ± 9.3 |

[a]Mean of five replicates, 80 females per replicate.

Results of the three previous tests indicate that, in terms of attraction and food consumption, Mazoferm 802 is preferred over NuLure. This important fact was not noticed by the various workers in their protein bait-malathion applications because, though NuLure may not be very attractive, the frequency of a fly encountering a droplet is great in ultralow-volume aerial applications, which deposit≈10 8-µ droplets of the formulation per meter square. In addition, as long as flies walked on, tasted, or ate the malathion bait, the flies died. However, now that researchers have tried to introduce a new third generation of insecticides to control fruit flies, gustatory behavior patterns of fruit flies have come to the forefront. Acceptability of a food bait is even more important when the effect of a latent toxicant, such as a photoactive dye, depends on total consumption and physiological uptake.

LETHALITY OF SOME PHOTOACTIVE DYES ALONE OR WITH ADJUVANTS

The following tests were set-up to determine acceptability of the developed Mazoferm formulation with the incorporation of a photoactive dye, phloxine B. We chose to feed flies under subdued light (8 µmol $s^{-1}$ $m^{-2}$) because the Mexican fruit fly does not feed in the dark and in nature feeds shortly after daybreak until it gets hot (≈32° C.) or start feeding much later depending on temperature. In our first test we chose to test concentrations of 0 (control, Mazoferm-fructose formulation only), 0.25, 0.5, 1, 2, and 4% phloxine B (92% Al: Active Ingredient) (Hilton Davies, Cincinnati, Ohio) because we had no idea about the relative activity of this dye in the Mazoferm-fructose formulation. Twenty female flies per cage were exposed to food treatments (five replicates per treatment) for 24 h and consumption measurements conducted as before. The following day, cages containing the flies were taken outside of the laboratory and exposed to natural sunlight for a period of four hours. The number of flies killed during that period was recorded every hour.

The results of this test are shown in Table 15. Temperature at the start of the test was 25° C. and the sky was mostly clear with patchy clouds. Minimum energy reading inside the cage, against the screen where flies rested, was 720 µmol $s^{-1}$ $m^{-2}$ half an hour after the beginning of the test and a maximum of 2100 µmol $s^{-1}$ $m^{-2}$ intermittently between cloud shadows. For the last hour of recording there were no clouds in the sky. As can be seen from the table. the percentage of females killed was dosage dependent. At a concentration of 4% phloxine B. some females were dying within 15 min of exposure to sunlight. At lower concentrations flies took longer to die. It appeared that acute light activated reactions started to level off after 3 h of exposure to sunlight at concentrations above 0.5% phloxine B. However after 4 h, it also appears that accumulated death at 0.5% concentration was as effective as higher concentrations. Nonetheless, this concentration appears to be at the margins of acute light-activated reactions.

TABLE 15

Sunlight-activated Death (Mostly Clear Sky) of Female
A. ludens After Exposing Them for 24 h to a Mazoferm Diet Containing
Various Concentrations of Phloxine B

| % Concn | Mean* (±SEM) Percentage Females Dead in Hour: | | | |
|---|---|---|---|---|
| | 1 | 2 | 3 | 4 |
| 0 | 3 ± 2.0 | 4 ± 2.9 | 5 ± 3.0 | 6 ± 3.7 |
| 0.25 | 11 ± 4.6 | 28 ± 3.0 | 62 ± 7.5 | 79 ± 7.0 |
| 0.5 | 8 ± 2.0 | 38 ± 7.2 | 67 ± 2.6 | 93 ± 2.0 |
| 1 | 37 ± 4.1 | 74 ± 8.1 | 87 ± 4.1 | 98 ± 1.3 |
| 2 | 49 ± 6.2 | 90 ± 3.5 | 96 ± 2.5 | 99 ± 1.0 |
| 4 | 98 ± 1.2 | 100 ± 0.0 | 100 ± 0.0 | 100 ± 0.0 |

*Mean of five replicates, 20 females per replicate.

Effective concentrations of phloxine B in Mazoferm-fructose formulations are 0.5% to 4% phloxine B. Table 16 describes percentage concentrations of phloxine B, the food consumption and percentage of flies killed over a four hour period. The test indicates that 0.5% phloxine B is only marginally effective.

TABLE 16

Food Consumption and Sunlight-activated Death (Mostly Cloudy Sky)
of Female A. ludens After Exposing Them for 24 h to a Mazoferm
Diet Containing Various Concentrations of Phloxine B

| % Concn | Mean* (±SEM) Food Consumption (mg) | Mean* (±SEM) Percentage Killed by Hour: | | |
|---|---|---|---|---|
| | | 1 | 2 | 4 |
| 0 | 105.7 ± 11.3 | 0 ± 0.0 | 0 ± 0.0 | 3 ± 1.4 |
| 0.25 | 92.9 ± 5.1 | 0 ± 0.0 | 10 ± 3.2 | 53 ± 14.4 |
| 0.5 | 93.5 ± 5.9 | 0 ± 0.0 | 7 ± 2.6 | 70 ± 2.7 |
| 1 | 104.4 ± 11.3 | 0 ± 0.0 | 20 ± 2.7 | 93 ± 1.2 |
| 2 | 98.4 ± 4.1 | 1 ± 1.0 | 34 ± 4.3 | 96 ± 1.0 |
| 4 | 95.8 ± 5.6 | 18 ± 4.8 | 71 ± 7.9 | 99 ± 0.8 |

*Mean of five replicates, 20 females per replicate.

We chose to examine the possibility of enhancing fly mortality by incorporating the nonphototoxic uranine (75% AI) (sodium salt of fluorescein) (Hilton Davis, Cincinnati, Ohio 45237) to our formulation containing 0.5% phloxine B. This concentration was chosen because in the two previous tests it appeared to approximate acute light-activated reactions. To a dye-bait formulation containing 0.5% phloxine B we added 0, 0.1, 0.2, 0.3 and 0.4% uranine and compared the consumption of each concentration to our base formulation of Mazoferm-fructose (check). Again, consumption is very similar for all uranine which did not enhance fly kill.

A composition envisioned by this invention provides an enhanced composition containing Mazoferm-fructose, phloxine B and uranine as an additive.

In a continued effort to improve onset of insect mortality and increase toxicity at lower dosages of phloxine B, the inventors hypothesized that if they could somehow increase gut membrane permeability, the effectiveness of the dye could be increased. The inventors have found that the addition adjuvants in the form of surface-active agents to various photoactive dye formulations enhanced their activity. A surface active agent found to be particularly effective was SM-9 (a proprietary blend of linear secondary alcohols reacted with ethylene oxide 99.97% AI: SMI, Valdosta, Ga.).

The inventors selected a test concentration of 0.5% phloxine B to which SM-9 was added. The treatments were check (Mazoferm-fructose formulation with 0.1% SM-9 as an emulsifier), and the concentration of 0.1, 0.25, 0.5, and 2% SM-9 in the phloxine B formulation. The test was conducted with young and mated female flies.

Data shown in Table 17 suggest that the addition of SM-9 greatly enhances the lethal effect of phloxine B on flies. In the first test (sunny day) with young females at concentrations of 1 and 2%, females started dying within five minutes of exposure to sunlight. All flies were killed in 1 h at the two highest concentrations. By the end of the second hour, nearly 100% of flies were killed at concentrations of 0.5% SM-9 and above. The rate of fly kill for the check and 0.25% SM-9 was about the same for the second and third hour. No flies were killed in the control during the entire test period. Compared to the concentration of 0.1% SM-9, fly kill was definitely accelerated by increasing amounts of SM-9. The same can be said for results obtained with mated females and singly-fed young females. A 100% kill was not observed in the first hour in the latter two tests because the initial energy impinging on these test flies was not as high (at least 100 µmol $s^{-1}$ $m^{-2}$) as that impinging on test insects of the first test. However, by the end of the second hour fly kill was over 90% at concentrations of 1 and 2%. There appears to be a slight lag with singly-fed flies but this lag may be attributed to the degree of metabolized dye in insect tissues rather than energy intensity. At a concentration of 0.1% of singly-fed flies there was a lag of four hours before substantial kill was observed.

A test was carried out to determine whether SM-9 itself had insecticidal activity. SM-9 was included in a Mazoferm-fructose bait. The treatments were check (base formulation), 0.25, 0.5, 1, 2, and 4% SM-9 in the base formulation. Flies were fed on their respective diets for 10 days. Death rate was 4, 3, 5, 0, 3 and 5%, for the respective concentrations in 10 days. Thus indicating that SM-9 is not innately toxic.

TABLE 17

Sunlight-Activated Death of Female *A. ludens* 24 hours (Except Single Feeding) After Exposing Them to a Mazoferm-Fructose Diet Containing 0.5% Phloxine B and Varying Amounts of the Adjuvant SM-9

| | Mean[a] (±SEM) Cumulative Percentage Killed by Indicated Hour. | | | | | | | | |
|---|---|---|---|---|---|---|---|---|---|
| % Concn | Young Females | | | Mated Females | | | Single Feeding[b] of Young Females | | |
| SM-9[c] | 1 | 2 | 3 | 1 | 2 | 4 | 1 | 2 | 4 |
| Check | 0 ± 0.0 | 0 ± 0.0 | 0 ± 0.0 | 0 ± 0.0 | 0 ± 0.0 | 0 ± 0.0 | 0 ± 0.0 | 0 ± 0.0 | 0 ± 0.0 |
| 0.1 | 11 ± 1.0 | 81 ± 3.3 | 100 ± 0.0 | 4 ± 1.9 | 55 ± 6.9 | 95 ± 5.0 | 0 ± 0.0 | 4 ± 1.9 | 74 ± 1.9 |
| 0.25 | 29 ± 6.0 | 82 ± 6.0 | 98 ± 0.0 | 3 ± 1.2 | 63 ± 6.2 | 99 ± 1.0 | 2 ± 1.2 | 31 ± 6.2 | 85 ± 4.5 |
| 0.5 | 67 ± 6.0 | 99 ± 1.0 | 100 ± 0.0 | 42 ± 5.6 | 95 ± 2.7 | 99 ± 1.0 | 3 ± 1.2 | 71 ± 4.0 | 91 ± 4.0 |
| 1 | 100 ± 0.0 | 100 ± 0.0 | 100 ± 0.0 | 66 ± 4.8 | 100 ± 0.0 | 100 ± 0.0 | 44 ± 5.3 | 91 ± 4.0 | 99 ± 1.0 |
| 2 | 100 ± 0.0 | 100 ± 0.0 | 100 ± 0.0 | 81 ± 4.3 | 100 ± 0.0 | 100. ± 0.0 | 75 ± 4.7 | 97 ± 2.0 | 100 ± 1.9 |

[a]Mean of five replicates, 20 females per replicate.
[b]Females were allowed to feed once, transferred to test cages, and 1 h after observed first feed taken out to sunlight.
[c]Check contained 0.1% SM-9 but no dye.

The inventors have conducted further tests (Table 18) to determine the effectiveness of phloxine B with a variety of adjuvants and they have compared the effectiveness of phloxine B vis-a-vis other candidate photoactive dyes. In the tests a concentration of 0.0382% was used because 0.0382% was the $LC_{50}$. A standard formulation consisted of 70% Mazoferm, 20% fructose, 1% SM-9 and 0.0382% phloxine B in water at a pH of 3.8.

Candidate photoactive test dyes contained the same formulation except that phloxine B was substituted with equivalent concentration dye. By taking this approach we could only see phototoxicity in those compounds that were as active or more so than phloxine B. Thus, in two different tests we evaluated the phototoxicity of methylene blue, rhodamine B, erythrosine B, and mercurochrome (SIGMA), brilliant blue BMA and eosin Y (Allied Chemical, Morristown, N.J.), fast green (Eastman Organic Chemicals, Rochester, N.Y.), and rose bengal (ICN Biochemicals, Cleveland, Ohio). Procedures in these tests were the same as those previously described.

The results of these tests (Table 18) show that rose bengal, erythrosine B, and eosin Y are sufficiently photoactive to kill flies at the concentrations tested. Erythrosine B is the most phototoxic, rose bengal about as active as phloxine B and eosin Y about half as active as phloxine B. The compounds are structurally related and their activity appears to be influenced by the presence of chlorine in the phthalic ring. Phloxine B and eosin Y have tetrabrominated xanthene rings with no chlorine in the latter, yet, it is half as active as phloxine B. Rose bengal and erythrosine B have tetraiodized xanthene rings with no chlorine in the latter, yet, it is almost twice as active as the former or phloxine B. Perhaps their activity is related to the specific halogen on the xanthene ring or a combined effect with that of the phthalic ring. We did not see any activity on the Mexican fruit fly with rhodamine B or methylene blue. However, the inventors do not wish to be bound by any theory of operation.

TABLE 18

Sunlight-activated Death of Female *A. ludens* After Exposing them 24 h to a Mazoferm Diet Containing 0.0382% Concentration of Various Dyes

| | | Mean[a] (±SEM) Percentage Killed | |
|---|---|---|---|
| Dye | C.I. Number | Test 1 | Test 2 |
| Check | — | 0 ± 0.0 a | 0 ± 0.0 a |
| Phloxine B (Stand.) | 45410 | 53 ± 6.3 b | 98 ± 1.2 c |
| Methylene Blue | 52015 | 0 ± 0.0 a | — |
| Rhodamine B | 45170 | 0 ± 0.0 a | — |
| Rose Bengal | 45440 | 51 ± 8.9 b | — |
| Erythrosine B | 45430 | 94 ± 1.9 c | — |
| Brilliant Blue BMA | — | — | 0 ± 0.0 a |
| Fast Green | 42053 | — | 0 ± 0.0 a |
| Mercurochrome | — | — | 3 ± 1.2 a |
| Eosin Y | 45380 | — | 41 ± 4.0 b |

[a]Mean of five replicates, 20 females per replicate. Means in same column followed by the same letter are not significantly different (p = 0.05; Fisher's Protected LSD)

The inventors have tested adjuvants and used the previous formulation containing 0.0382% phloxine B. Where indicated, they substituted 1% AI SM-9 with the appropriate test adjuvant at equivalent concentration. In addition, one test was conducted using 1% soybean oil in conjunction with some of the adjuvants to see if we could enhance the lethality of phloxine B. The inventors tested the following adjuvants: MICRO (a laboratory cleaner, International Products Corporation, Burlington, N.J.), Silwet L-77 (99% AI, copolymer surfactant, Union Carbide Chemicals & Plastic Co. Inc., Danbury, Conn.), Triton X-100 (99% AI, polyoxyethylene ethers and other surface active compounds, SIGMA), Kinetic (99% AI, blend of polyalkyleneoxide modified polydimethylsiloxane) and Citrufilm (99% AI, paraffin base petroleum oil) (Helena Chemical Company, Memphis, Tenn.), Latron AG-98 (80% AI, alkyl aryl polyoxyethylene, Rohm and Haas Company, Philadelphia, Pa.), and NuFilm P (96% AI, poly-1-p-menthene) and NuFilm 17 (96% AI, di-1-p-menthene) (Miller Chemical & Fertilizer Corporation, Hanover, Pa.).

The results in Table 19 show that in the first test (conducted during a sunny day), SM-9, Silwet L-77, Triton X-100 and Kinetic were about equally as effective in increasing fly mortality. However, during the first hour only Kinetic significantly killed more adults (67±8.9%) than any of the other adjuvants over the check (0%). The second test was conducted during a cloudy, hazy day with an energy flux of 80 to 170 µmol s$^{-1}$ m$^{-2}$ for the first three hours of the experiment and the last hour turning sunny. Nonetheless, in this test Latron AG-98 and Citrufilm were significantly more effective than the standard SM-9. For the third test each of the most promising adjuvants was combined with soybean oil in Mazoferm-fructose formulation and fed to flies. Twenty-four hours later fly exposure to sunlight was conducted during a cloudy day. The energy flux during the exposure period was from 100 to 300 µmol s$^{-1}$ m$^{-2}$. The results show that, in fact, soybean oil enhances the phototoxicity of phloxine B. The addition of soybean oil to formulations with SM-9, Kinetic, and Latron Ag-98 significantly killed more flies in comparison to the standard (with 1% SM-9). However, the addition of soybean oil to Citrufilm adversely affected the proven additive effects of Citrufilm. This implies that the active ingredients (polyoxyethylated polyol fatty acid esters, 99%) of Citrufilm were incompatible with soybean oil (a vegetable oil) but we need to remember that the data were taken at different conditions. The total amount of energy is about the same but the dose-rate and irradiation time are quite different.

TABLE 19

Effect of a 1% Adjuvants on Sunlight-activated Death of Female *A. ludens* After Exposing Them for 24 h to a Mazoferm-Fructose Formulation Containing 0.0382% Phloxine B

| | Mean[a] (±SEM) Percentage Killed in: | | |
|---|---|---|---|
| Adjuvant | Test 1,2 h | Test 2,4 h | Test 3[b] 2 h |
| Check | 3 ± 0.0 a | 4 ± 2.5 a | 2 ± 1.2 d |
| SM-9 (Standard) | 91 ± 4.6 c | 64 ± 7.8 c | 77 ± 4.1 c |
| Micro | 35 ± 5.0 b | — | — |
| Silwet L-77 | 74 ± 13.3 c | — | — |
| Triton X-100 | 88 ± 4.4 c | — | — |
| Kinetic | 99 ± 1.0 c | — | 100 ± 0.0 a |
| NuFilm 17 | | 10 ± 5.2 a | — |
| NuFilm P | | 38 ± 12.0 b | — |
| Latron AG-98 | | 83 ± 5.8 d | 95 ± 2.2 ab |
| Citrufilm | | 86 ± 2.9 d | 73 ± 4.6 c |

[a]Mean of five replicates, 20 females per replicate. Means in same column followed by the same letter are not significantly different ($p = 0.05$; Fisher's Protected LSD.)
[b]In addition to 1% adjuvant, treatments contain 1% soybean oil, except the standard.

The addition of phloxine B with/without uranine to the base Mazoferm formulation did not deter the Mexican fruit fly from feeding according to our results. However, the addition of adjuvants dramatically increased fly mortality in our formulated preparation. The addition of adjuvants, so far as known by the inventors, has never been reported with the use of malathion-bait sprays. Adjuvants to specifically facilitate penetration of the dye from the gut tract into the body tissues of the insect. The prior art has used dispersants with their dye formulation to increase the dispersion of their test material in water but no one has reported the use of the inventors' specific combination of dye and adjuvant formulations. The sensitivity of the Mexican fruit fly to the photooxidants erythrosine B, phloxine B, rose bengal, and eosin Y usinc $LC_{50}$ equivalent concentrations showed that erythrosine B is the most effective followed by phloxine B and rose bengal being nearly equal, and eosin Y about half as active as phloxine B. The study with adjuvants also showed that fly kill could be improved, at the same dye concentration, and that with the addition of an appropriate vegetable oil this kill could be further enhanced.

IMPROVEMENTS ON ATTRACTIVENESS OF FORMULATION

There is always a concern that with the addition of chemicals the desirable qualities of the product may change. In our case the inventors established that Mazoferm and NuLure both have attractive qualities to the flies. Mazoferm was found to be more attractive than NuLure in two of the tests but with the addition of 0.5% phloxine B the inventors did not know whether this had changed. The inventors set-up a test to determine the relative attraction of 30% Mazoferm or NuLure with and without dye and at 70% with dye. Procedures were the same as those previously described for laboratory attraction tests. The results show that though Mazoferm with dye did not lose any attraction in relation to Mazoferm without dye, there was a significant decrease in attraction in NuLure when dye was added to it. There was no reason for this change that we could detect; even pH range was fairly stable (4 to 4.1) for NuLure. The pH range for Mazoferm was from 3.78 to 3.83. Mazoferm may be more attractive than NuLure at lower pHs.

Mazoferm was shown to be a more acceptable food to flies than NuLure and ostensibly its gustatory appeal and attraction to flies of Mazoferm is not lost with the addition of phloxine B; however, the inventors questioned this status when the adjuvant SM-9 and soybean oil were added. Therefore, they conducted an attractants test with the Mazoferm-base formulation at concentrations of 10, 40, and 70% Mazoferm against same concentrations with the addition of 0.5% phloxine B, 1% SM-9, and 1% soybean oil. Procedures were the same as already described. The results of the test indicated that there was no loss in attraction by the addition of phloxine B, SM-9, and soybean oil. In fact, there was a significant increase in attraction of Mazoferm-base with additives over that with none at the 10% Mazoferm concentration. The mean (±SEM) fly response was 37.2 (1.2), 43.2 (2.7), and 41.6 (2.2) with and 30.1 (1.5), 35.7 (2.1), and 37 (2.8) without additives for concentrations of 10, 40 and 70% Mazoferm, respectively. The response profile indicates a slight increase in attraction of Mazoferm with additives over that with none but it could be that under the conditions of the test the added attraction can be attributed to differences in color of the treatments. The color of the Mazoferm-fructose formulation is amber and with 0.5% phloxine B is dark red. Other experiments when using plastic panels, found that black, red, blue, and white were not more attractive than colorless control panels. Thus, indicating that color is not a confounding factor. The important aspect of this test is that no loss in attraction was observed despite all the additives.

The inventors have found that acetic acid in their formulations increases effectiveness by being an attraction enhancer. A typical formulation comprised Mazoferm bait with 0.5% phloxine B, 1% SM-9 and 1% soybean oil and 0.6% acetic acid, with a pH in the range of 3.66–4.0. Other concentrations of acetic acid found operative were 0.075, 0.15, 0.3, 0.6 and 1.2%. It is believed that up to 2% would be operative.

The idea of using ultralow-volume (≈1 liter/hectare) bait sprays with large droplets (≈1–2 mm diam) is that each droplet is a center of attraction to which flies will respond. They should find the source phagostimulatory and feed ad libitum. In this manner, one can deliver the intended toxicant without repelling the flies. To this end one should be able to increase the attractiveness of the food source.

The inventors have also found the adjuvants, Kinetic, Latron AG-98, and Citrufilm, to be as good or better than SM-9 in inducing fly mortality in conjunction with phloxine B. The addition of soybean oil further enhanced the activity of SM-9, Kinetic, and Latron AG-98. Of the three, Kinetic appears to be the most promising because it induces the most rapid kill.

Tests have also indicated that with the addition of phloxine B, SM-9, and soybean oil to the Mazoferm-fructose base no attraction is lost. Flies respond about the same to a formulation with or without additives and that the quality of the Mazoferm-fructose mixture is quite stable and remains so despite the other additions.

The bait can be used for ultralow-volume aerial applications. The results show that the compositions can go as low as 40% Mazoferm without losing the attractive Mazoferm. Conventional ground spray equipment can be used to apply to lower 40% concentration of Mazoferm. If the formulation needs to be thickened, it can be done with ease with the addition of xanthan gum. This gum dissolves readily in water at room temperature.

The inventors propose that the formulation of 70% Mazoferm 802, 20% fructose or invert sugar, 0.1 to 1% phloxine B, 1% SM-9 or equivalent adjuvant, 1% soybean oil, 0.6% acetic acid, and optionally 0.4 to 1% xanthan gum, volume to volume or weight to volume in water makes an attractive, phagostimulatory dye-bait that can be used not only for Mexican fruit fly but for other fruit flies such as the Mediterranean fruit fly and other fruit flies of the family Tephritidae. The inventive composition is an environmentally safe formulation and most of the products (excepting SM-9), are already used for human or animal consumption. The linear alcohols in SM-9 are generally safe and for that reason are used as adjuvants. The residual activity of phloxine B is not perceived to be long, as it is degraded rapidly by sunlight and will not affect nontarget organisms unless attracted to and consume the dye-bait formulation. There is no toxic contact activity with phloxine B as is the case with malathion.

Mazoferm is a better attractant than NuLure and is less expensive. In these studies flies were more attracted to and consumed more Mazoferm and lived longer than flies provided with NuLure. Thus, indicating that Mazoferm is an outstanding candidate to replace NuLure in a bait. In our composition the Mazoferm functions as both a bait and attractant whose activity is enhanced by the use of adjuvants.

The invention herein described has involved Mazoferm which is a commercially available enzymatically hydrolyzed protein; however, other enzymatically hydrolyzed corn proteins would be operative and accordingly this invention should not be limited to Mazoferm.

In the disclosed invention a broad array of photoactive dyes have been shown to be effective in killing the Mexican fruit fly. In the preferred composition phloxine B was employed, although other photoactive dyes would be operative. Phloxine B has been shown to be effective at a concentration 0.382% to 4% of the total composition, although operative ranges outside of these parameters could readily be determined by those skilled in the art. Mazoferm in a percentage range of 10%–70% of total composition has been tested with the optimum amount being. Sugar has been included in the composition in amounts of 4 to 24%. Adjuvants, and particularly SM-9 has been included in the composition in a range of 0.1–4%. Soybean oil as a feeding enhancer and antifoaming agent has been included in the composition in a broad range of 0.1–4% and narrow range of 0.5 to 1.5%. Soybean oil has been included in a preferred range of 1%. Of course, it is understood that other vegetable oils would be operative. Acetic acid at 0.6% has been included, however ranges of 0.0075% to 1.2% have been tested. Xanthan gum 0.4–1.5% as a thickener has been incorporated in a range of 0.5 to 1.5% with 0.5% being preferred. Other thickeners known in the art would be operative. The preferred pH of the composition is pH 3.78–3.83 with the broad range being pH 3.7–9. The balance of the composition being water.

An important ingredient of the insecticidal composition of this invention is polyethylene glycol or polypropylene glycol or like glycol which are to function as antifoaming agents, as well as moisturizers once the composition is sprayed onto plants. For purposes of antifoaming action, only a small amount of, for example, 0.25% of polyethylene glycol is required. For moisturization a range of 0.25 to 1.5% is operative, while 1% is preferred. As with other percentage ranges employed herein, the ranges can be varied by those skilled int he art familiar with insecticidal formulations.

A composition of effective amounts of phloxine B and uranine would be useful in the compositions of the disclosed invention, and would be effective in killing insects of the Tephritidae family and particularly the Mexican fruit fly.

It is to be understood that specific effective amounts of the components of the composition have been set forth to disclose the best-mode known to inventors for carrying out the disclosed invention. However, these ranges can be varied and other effective ranges determined by routine experiments by workers skilled in the art.

In its broadest aspects this invention involves an insecticidal composition comprising effective amounts of a photoactive dye and hydrolyzed protein. The composition can further contain sugar therein. The insecticidal composition containing the photoactive dye can contain an effective adjuvant therein for enhancing insecticidal activity. A preferred composition contains the photoactive dye, phloxine B, the hydrolyzed protein is enzyme, hydrolyzed corn protein and the adjuvant, SM-9. In addition the composition can contain added soybean oil, acetic acid, and xanthan gum. The insecticidal composition is primarily for killing the Mexican fruit fly but can also be used effectively for killing members of the family Tephritidae and comprises effective amounts of a photoactive dye, hydrolyzed corn protein, sugar, an effective adjuvant, soybean oil, acetic acid and optionally a xanthan gum. A specific insecticidal composition for killing the Mexican fruit fly comprises a toxic formulation of 70% Mazoferm 802, 20% fructose or invert sugar, 0.1 to 1% phloxine B, 1% SM-9 or equivalent adjuvant, 1% soybean oil, 0.6% acetic acid, and optionally 0.4 to 1% xanthan gum, volume to volume or weight to volume in water, said composition making an attractive, phagostimulatory photoactive dye-bait.

A broad insecticidal composition of this invention for killing the Mexican fruit fly comprises effective amounts of a enzyme hydrolyzed corn protein and a photoactive dye. More specifically composition can contain phloxine B and the corn hydrolyzate, Mazoferm. This invention involves an insecticidal method for killing fruit flies of the family Tephritidae and specifically the Mexican fruit fly comprising applying to the habitat of said fruit fly effect amounts corn protein hydrolyzate and photoactive dye, and more specifically the hydrolyzate is Mazoferm and the photoactive dye is phloxine B. Contemplated by this invention is an insecticidal composition comprising effective amounts of a phloxine B photoactive dye;

a hydrolyzed corn bait attractant; and an adjuvant selected from the group consisting of SM-9, Tween 60, Sylgard and Kinetic.

The photoactive dye is present in an amount of between 0.025%–4.0% by weight of said composition. A broad composition of this invention comprises an insecticidal composition intended to be consumed by an insect comprising:

at least one photoactive dye;

a selected attractant compound to cause the insect to ingest the composition; and an adjuvant to alter the toxicity of the composition once ingested by the insect.

The composition can contain a feeding stimulant substituted for said selected attractant compound or the composition can contain an attractant and a feeding stimulant.

A specific insecticidal composition of this invention comprises effective amounts of:

0.382–4% a photoactive dye,

10–70% Mazoferm,

4–24% sugar, 0.1–4% SM-9 or Tween 60, 0.25–1.5% an antifoaming agent and moistening agent, 0.5–1.5% vegetable oil attractant, 0.5–1.5% a gum thickening agent and an acid attractant and 0.0075 to 1.2% acid attractant An optimum composition developed to kill fruit flies of the genus Anastrepha is as follows:

| Ingredients | % Concentration (V:V) | gm/ml/Liter |
| --- | --- | --- |
| Phloxine B (92%) | 0.5 | 5.4 |
| Mazoferm 802 | 70.0 | 700.0 |
| Invertose | 20.0 | 200.0 |
| Tween 60 (as formulated) | 1.0 | 10.0 |
| Soybean oil | 1.0 | 10.0 |
| Acetic acid | 0.6 | 6.0 |
| Polyethylene glycol 200 | 2.0 | 20.0 |
| Xanthan gm | 0.4 | 4.0 |
| Water | 4.5 | 45.0 |

In the optimum composition water has been set forth as the carrier, other liquid carriers could be formulated by those skilled in the art.

While the instant invention has been described in accordance with what is believed to be preferred and practical embodiments thereof, it is recognized that departures may be made within the spirit and scope of the following claims which are not to be limited except within the doctrine of equivalents.

Many benefits are to be derived from the insecticidal compositions of this invention. The compositions can not only be used for the Mexican fruit fly but for other fruit flies such as the Mediterranean fruit fly and other fruit flies of the family Tephritidae. In addition, it is an environmentally safe formulation and most of the products (excepting SM-9), are already used for human or animal consumption. The linear alcohols in SM-9 are generally safe and for that reason are used as adjuvants. The residual activity of phloxine B is not perceived to be long, since it is degraded rapidly by sunlight and will not affect nontarget organisms unless they are attracted to and consume the dye-bait formulation. There is no toxic contact-activity with phloxine B as is the case with malathion.

Methyl eosin is another photoactive dye which has been found to be a particularly effective insecticidal dye for killing the Mexican fruit fly. It can be employed in effective concentrations of six parts per billion to 2%. An operative concentration would be 0.1%. Other effective concentrations can be determined by routine experiment. The methyl eosin can be used in an enzyme hydrolyzed corn protein bait.

It has been found that the esters of the photoactive dyes can be used in producing insecticidal activity. The esters may be more stable under conditions of use than the unesterified compounds. The concentrations for use of the esters would approximate those of the unesterified dyes.

It is believed that other food drug and cosmetic grade dyes would be operative for use in this invention.

We claim:

1. An insecticidal method for killing fruit flies of the Tephritidae family comprising applying to the habitat of said fruit flies of the Tephritidae family an insecticidal composition comprising a phototoxically effective amount of a food-grade photoactive dye and an effective amount of enzyme hydrolyzed corn protein bait.

2. The insecticidal method of claim 1 wherein the fruit fly of the Tephritidae family is the Mexican fruit fly.

3. The method of claim 2 wherein the photoactive dye is phloxine B.

4. The method of claim 3 wherein uranine is added to the phloxine B.

5. An insecticidal composition for killing Tephritidae comprising effective amounts of phloxine B phototoxic photoactive dye;

an enzyme hydrolyzed corn protein bait attractant; and an adjuvant selected from the group consisting of alkyloxypolyethyleneoxyethanol of the chemical formula

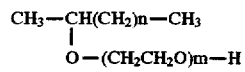

wherein n is from 9 to 15 and m is from 3 to 40, and poly oxyethylene-sorbitan monostearate.

6. The composition of claim 5 wherein said phototoxic photoactive dye is present in an amount of between 0.025%–4.0% by weight of said composition.

7. An insecticidal composition comprising in effective amounts to kill fruit flies of the Tephritidae family:

a food-grade phototoxic photoactive dye, enzyme hydrolyzed corn protein bait, sugar feeding stimulant, alkyloxypolyethyleneoxyethanol of the emical formula

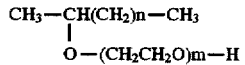

wherein n is from 9 to 15 and m is from 3 to 40, an antifoaming agent and moistening agent, vegetable oil attractant, a gum thickening agent and an acid attractant.

8. The insecticidal composition of claim 7 wherein the composition comprises 0.382–4% photoactive dye, 10–70% enzyme hydrolyzed corn protein, 4–24% sugar, 0.1–4% alkyloxypolyethyleneoxyethanol of the chemical formula

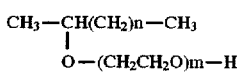

wherein n is from 9 to 15 and m is from 3 to 40, 0.25%–1.5% antifoaming and moistening agent,
0.5–1.5% vegetable oil attractant,
0.5–1.5% gum thickening agent and
0.0075 to 1.2% acid attractant.

9. The insecticidal composition of claim 8 wherein
the photoactive dye is phloxine B,
the antifoaming and moistening agent is polyethylene glycol,
the vegetable oil attractant is soybean oil,
the gum thickening agent is xanthan gum, and
the acid attractant is acetic acid.

10. An insecticidal composition comprising effective amounts to kill fruit flies of the Tephritidae family:
a food-grade phototoxic photoactive dye,
enzyme hydrolyzed corn protein bait,
sugar feeding stimulant,
polyoxyethylene-sorbitan monostearate adjuvant,
an antifoaming agent and moistening agent,
vegetable oil attractant,
a gum thickening agent and
an acid attractant.

11. The insecticidal composition of claim 10 wherein the composition comprises in effective amounts of:
0.382–4% food-grade phototoxic photoactive dye,
10–70% enzyme hydrolyzed corn protein bait,
4–24% sugar feeding stimulant,
0.1–4% polyoxyethylene-sorbitan monostearate adjuvant,
0.25%–1.5% antifoaming and moistening agent,
0.5–1.5% vegetable oil attractant,
0.5–1.5% gum thickening agent and
0.0075 to 1.2% acid attractant.

12. The method of claim 1 wherein the food-grade photoactive dye is methyl eosin.

13. The method of claim 1 wherein the food-grade photoactive dye is an ester.

14. An insecticidal composition for killing the Mexican fruit fly comprising a toxic formulation of 70% enzyme hydrolyzed corn protein bait, 20% fructose or invert sugar, 0.1 to 1% phloxine B, 1% alkyloxypolyethyleneoxyethanol of the chemical formula

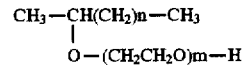

wherein n is from 9 to 15 and m is from 3 to 40, 1% soybean oil, 0.6% acetic acid, and optionally 0.4 to 1.5% xanthan gum, volume to volume or weight to volume in water, said composition making an attractive, phagostimulatory dye-bait.

* * * * *